(12) United States Patent
Yang et al.

(10) Patent No.: US 11,883,344 B2
(45) Date of Patent: Jan. 30, 2024

(54) NEURAL STIMULATION IN VITRO AND IN VIVO BY PHOTOACOUSTIC NANOTRANSDUCERS

(71) Applicant: Trustees of Boston University, Boston, MA (US)

(72) Inventors: Chen Yang, Newton, MA (US); Ji-Xin Cheng, Newton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 18/103,093

(22) Filed: Jan. 30, 2023

(65) Prior Publication Data

US 2023/0240935 A1 Aug. 3, 2023

Related U.S. Application Data

(60) Provisional application No. 63/305,863, filed on Feb. 2, 2022.

(51) Int. Cl.
*A61H 23/00* (2006.01)
*A61N 5/06* (2006.01)

(52) U.S. Cl.
CPC ........... *A61H 23/00* (2013.01); *A61N 5/0603* (2013.01); *A61H 2201/10* (2013.01); *A61N 2005/063* (2013.01); *A61N 2005/0659* (2013.01); *A61N 2005/0663* (2013.01)

(58) Field of Classification Search
CPC .. A61H 23/00; A61H 2201/10; A61N 5/0603; A61N 2005/063; A61N 2005/0659; A61N 2005/0663; A61N 7/00; A61N 5/067; A61N 2007/0026; A61N 2007/0073
See application file for complete search history.

(56) References Cited

U.S. PATENT DOCUMENTS

| | | | |
|---|---|---|---|
| 2012/0121712 A1 | 5/2012 | Ciofani et al. | |
| 2013/0324909 A1* | 12/2013 | Aydt | A61P 17/02 604/20 |
| 2017/0027645 A1* | 2/2017 | Ben Oren | A61B 18/22 |
| 2017/0080255 A1 | 3/2017 | Law et al. | |
| 2020/0077974 A1* | 3/2020 | Avanaki | A61B 8/085 |
| 2020/0246641 A1 | 8/2020 | Tyler | |

FOREIGN PATENT DOCUMENTS

| | | |
|---|---|---|
| CN | 103976709 A | 8/2014 |
| WO | WO 2005/093831 | * 10/2005 |

OTHER PUBLICATIONS

International Search Report and Written Opinion of International Application No. PCT/US2023/011857 dated Apr. 10, 2023.
(Continued)

*Primary Examiner* — Quang D Thanh
(74) *Attorney, Agent, or Firm* — Burns & Levinson LLP; Steven M. Mills

(57) ABSTRACT

An example photoacoustic system for neurostimulation includes a light producing device for producing light of a specific wavelength. At least one nanotransducer is binded on a surface of a neuron. The nanotransducer converts the light with the specific wavelength into at least one acoustic wave at or near the neuron.

30 Claims, 33 Drawing Sheets

(56) References Cited

OTHER PUBLICATIONS

Legon et al., "Transcranial focused ultrasound modulates the activity of primary somatosensory cortex in humans," Nature Neuroscience, vol. 17, No. 2, pp. 322-332, 2014.
Legon et al., "Transcranial focused ultrasound neuromodulation of the human primary motor cortex," Scientific Reports, vol. 8, No. 10007, pp. 1-14, 2018.
Lin et al., "Sonoporation-mediated gene transfer into adult rat dorsal root ganglion cells," Journal of Biomedical Science, vol. 17, No. 44, pp. 1-6, 2010.
Lo et al., "Imaging the extent of plasmon excitation in Au nanowires using pump-probe microscopy," Optics Letters, vol. 38, No. 8, pp. 1265-1267, 2013.
Luo et al., "Bis-isoindigos: New Electron-Deficient Building Blocks for Constructing Conjugated Polymers with Extended Electron Delocalization," Asian J. Org. Chem., pp. 1-8, 2018.
Lyu et al., "A Photolabile Semiconducting Polymer Nanotransducer for Near-Infrared Regulation of CRISPR/Cas9 Gene Editing" Angew. Chem. Int. Ed., vol. 58, pp. 18197-18201, 2019.
Lyu et al., "Semiconducting Polymer Nanobioconjugates for Targeted Photothermal Activation of Neurons," Journal of the American Chemical Society, vol. 138, pp. 9049-9052, 2016.
Maingret et al., "TRAAK Is a Mammalian Neuronal Mechano-gated K+ Channel," The Journal of Biological Chemistry, vol. 274, No. 3, pp. 1381-1387, 1999.
Matthews et al., "Pump-Probe Imaging Differentiates Melanoma from Melanocytic Nevi," Sci. Transl. Med., vol. 3, No. 71, pp. 1-19, 2011.
"Miao et al., ""Molecular afterglow imaging with bright, biodegradablepolymer nanoparticles,"" Nature Biotechnology, vol. 35, No. 11, pp. 1102-1115, 2017."
Mueller et al., "Transcranial Focused Ultrasound Modulates Intrinsic and Evoked EEG Dynamics," Brain Stimulation, vol. 7, pp. 900-908, 2014.
Parameswaran et al., "Photoelectrochemical modulation of neuronal activity with free-standing coaxial silicon nanowires," Nature Nanotechnology, vol. 13, pp. 260-266, 2018.
Park et al., "One-step optogenetics with multifunctional flexible polymer fibers," Nature Neuroscience, vol. 20, No. 4, pp. 612-621, 2017.
"Paviolo et al., ""Laser exposure of gold nanorods can induceintracellular calcium transients,"" J. Biophotonics, vol. 7, No. 10, pp. 761-765, 2014."
Perlmutter et al., "Deep Brain Stimulation," Annu. Rev. Neurosci., vol. 29, pp. 229-257, 2006.
Plaksin et al., "Intramembrane Cavitation as a Predictive Bio-Piezoelectric Mechanism for Ultrasonic Brain Stimulation," Physical Review X, vol. 4, pp. 1-10, 2014.
Plant et al., "TRPV4: A Multifunctional Nonselective Cation Channel withComplex Regulation," TRP Ion Channel Function in Sensory Transduction and Cellular Signaling Cascades, CRC Press, pp. 1-13, 2007.
Shi et al., "A fiber optoacoustic emitter with controlled ultrasound frequency for cell membrane sonoporation at submillimeter spatial resolution," Photoacoustics, vol. 20, pp. 1-10, 2020.
"Shibasaki et al., ""Effects of Body Temperature on Neural Activity in theHippocampus: Regulation of Resting Membrane Potentialsby Transient Receptor Potential Vanilloid 4,"" The Journal of Neuroscience, vol. 27, No. 7, pp. 1566-1575, 2007."
Thorneloe et al., "An Orally Active TRPV4 Channel Blocker Prevents and Resolves Pulmonary Edema Induced by Heart Failure," Science Translational Medicine, vol. 4, No. 159, pp. 1-12, 2012.
Tong et al., "Label-free imaging of semiconducting and metallic carbon nanotubes in cells and mice using transient absorption microscopy," Nature Nanotechnology, vol. 7, pp. 56-61, 2011.
Tufail et al., "Transcranial Pulsed Ultrasound Stimulates Intact Brain Circuits," Neuron, vol. 66, pp. 681-694, 2010.
Tufail et al., "Ultrasonic neuromodulation by brain stimulation with transcranial ultrasound," Nature Protocols, vol. 6, No. 9, 2011.
Tyler et al., "Ultrasonic modulation of neural circuit activity," Current Opinion in Neurobiology, vol. 50, pp. 222-231, 2018.
Uhlén et al., "Tissue-based map of the human proteome," Science, vol. 347, No. 6220, pp. 394-404, 2015.
Uhlén et al., "Towards a knowledge-based Human Protein Atlas," Nature Biotechnology, vol. 28, No. 12, pp. 1248-1250, 2010.
Wang, "Tutorial on Photoacoustic Microscopy and Computed Tomography," IEEE Journal of Selected Topics in Quantum Electronics, vol. 14, No. 1, pp. 171-179, 2008.
Wang, "Photoacoustic Imaging and Spectroscopy," CRC Press, Taylor & Francis Group, pp. 1-538, 2017.
Weissler et al., "Simulation of morphologically structured photothermal neural stimulation," Journal of Neural Engineering, vol. 14, pp. 1-8, 2017.
Wu et al., "Contrast Agents for Photoacoustic and Thermoacoustic Imaging: A Review," International Journal of Molecular Sciences, vol. 15, pp. 23616-23639, 2014.
Wu et al., "Functionalized NIR-II Semiconducting Polymer Nanoparticles for Single-cell to Whole-Organ Imaging of PSMA-Positive Prostate Cancer," Small, pp. 1-13, 2020.
Wu et al., "Polymer Electrochromism Driven by Metabolic Activity Facilitates Rapid and Facile Bacterial Detection and Susceptibility Evaluation," Adv. Func. Mater., pp. 1-10, 2020.
Wu et al., "Semiconducting Polymer Nanoparticles for Centimeters-Deep Photoacoustic Imaging in the Second Near-Infrared Window," Advanced Materials, pp. 1-6, 2017.
Yamilov et al., "Position-Dependent Diffusion of Light in Disordered Waveguides," Physical Review Letters, vol. 112, pp. 1-5, 2014.
Yizhar et al., "Optogenetics in Neural Systems," Neuron, vol. 71, pp. 9-34, 2011.
Yong et al., "Gold-Nanorod-Assisted Near-Infrared Stimulation of Primary Auditory Neurons," Advanced Healthcare Materials, vol. 3, pp. 1862-1868, 2014.
Yoo et al., "Focused ultrasound excites neurons via mechanosensitive calcium accumulation and ion channel amplification," bioRxiv, pp. 1-15, 2020.
Yoo et al., "Single-Cell Photothermal Neuromodulation for Functional Mapping of Neural Networks," ACS Nano, vol. 13, pp. 544-551, 2019.
Yu et al., "Near-Infrared-Light Activatable Nanoparticles for Deep-Tissue-Penetrating Wireless Optogenetics," Advanced Healthcare Materials, vol. 8, pp. 1-11, 2019.
Yue et al., "Magneto-Electric Nano-Particles for Non-Invasive Brain Stimulation," PLoS One, vol. 7, No. 9, pp. 1-5, 2012.
Zhang et al., "Cellular Binding and Internalization of Functionalized Silicon Nanowires," Nano Lett., vol. 12, pp. 1002-1006, 2012.
Zhang et al., "Optogenetic interrogation of neural circuits: technology for probing mammalian brain structures," Nature Protocols, vol. 5, No. 3, pp. 439-456, 2010.
Zhu et al., "Transient absorption microscopy: Technological innovations and applications in materials science and life science," J. Chem. Phys., vol. 152, pp. 1-15, 2020.
Zhu et al., "Ultrafast Dynamic Microscopy of Carrier and Exciton Transport," Annu. Rev. Phys. Chem., vol. 70, pp. 219-244, 2019.
"All et al., ""Expanding the Toolbox of Upconversion Nanoparticlesfor In Vivo Optogenetics and Neuromodulation,"" Advanced Materials, pp. 1-15, 2019."
Ao et al., "An Upconversion Nanoparticle Enables Near Infrared-Optogenetic Manipulation of the Caenorhabditis elegans Motor Circuit," ACS Nano, vol. 13, pp. 3373-3386, 2019.
Aryal et al., "MRI monitoring and quantification of ultrasound-mediated delivery of liposomes dually labeled with gadolinium and fluorophore through the blood-brain barrier," Ultrasound in Med. & Biol., vol. 45, No. 7, pp. 1733-1742, 2019.
Aryal et al., "Ultrasound-mediated delivery ofgadolinium and fluorescent-labeledliposomes through the blood-brain barrier," J. Acoust. Soc. Am., vol. 139, No. 2093, pp. 1-2, 2016.
Bagriantsev et al., "Piezo Proteins: Regulators of Mechanosensation and Other Cellular Processes," The Journal of Biological Chemistry, vol. 289, No. 46, pp. 31673-31681, 2014.

(56) References Cited

OTHER PUBLICATIONS

Beane et al., "Ultrafast measurements of the dynamics of single nanostructures: a review," Reports on Progress in Physics, vol. 82, pp. 1-31, 2019.

Brohawn et al., "Mechanosensitivity is mediated directly by the lipid membrane in TRAAK and TREK1 K+ channels," Proceedings of the National Academy of Sciences of the United States of America, vol. 111, No. 9, pp. 3614-3619, 2014.

Brohawn et al., "Physical mechanism for gating and mechanosensitivity of the human TRAAKK+ channel," Nature, vol. 516, pp. 126-140, 2014.

Brunoni et al., "Clinical research with transcranial direct current stimulation (tDCS): Challenges and future directions," Brain Stimulation, pp. 175-195, 2012.

Canales et al., "Multifunctional fibers for simultaneous optical, electrical and chemical interrogation of neural circuits in vivo," Nature Biotechnology, vol. 33, No. 3, pp. 277-286, 2015.

Carvalho-de-Souza et al., "Cholesterol Functionalization of Gold Nanoparticles Enhances Photoactivation of Neural Activity," ACS Chem. Neurosci., vol. 10, pp. 1478-1487, 2019.

Carvalho-de-Souza et al., "Optocapacitive Generation of Action Potentials by Microsecond Laser Pulses of Nanojoule Energy," Biophysical Journal, vol. 114, pp. 283-288, 2018.

Carvalho-de-Souza et al., "Photosensitivity of Neurons Enabled by Cell-Targeted Gold Nanoparticles," Neuron, vol. 86, pp. 207-217, 2015.

Chang et al., "Narp regulates homeostatic scaling of excitatory synapses on parvalbumin-expressing interneurons," Nature Neuroscience, vol. 13, No. 9, pp. 1090-1097, 2010.

Chen et al., "Label-Free Imaging of Heme Dynamics in Living Organisms by Transient Absorption Microscopy," Analytical Chemistry, vol. 90, pp. 3395-3401, 2018.

Chen et al., "Near-infrared deep brain stimulation via upconversion nanoparticle-mediated optogenetics," Science, vol. 359, pp. 679-684, 2018.

"Chen et al., ""Volumetric chemical imaging by stimulated Ramanprojection microscopy and tomography,"" Nature Communications, vol. 8, No. 15117, pp. 1-12, 2017."

Chen et al., "Wireless magnetothermal deep brain stimulation," Science, pp. 1-7, 2015.

Cook et al., "Tissue-mimicking phantoms for photoacoustic and ultrasonic imaging," Biomedical Optics Express, vol. 2, No. 11, pp. 3193-3206, 2011.

Coste et al., "Piezo1 and Piezo2 Are Essential Components of Distinct Mechanically Activated Cation Channels," Science, vol. 330, pp. 55-61, 2010.

Dante et al., "Selective Targeting of Neurons with Inorganic Nanoparticles: Revealing the Crucial Role of Nanoparticle Surface Charge," ACS Nano, vol. 11, pp. 6630-6640, 2017.

De Boer et al., "Neuronal photoactivation through secondharmonic near-infrared absorption by gold nanoparticles," Light: Science & Applications, vol. 7, No. 100, pp. 1-13, 2018.

Deffieux et al., "Low-Intensity Focused Ultrasound Modulates Monkey Visuomotor Behavior," Current Biology, vol. 23, pp. 2430-2433, 2013.

Dong et al., "Label-free quantitation of glycated hemoglobin in single red blood cells by transient absorption microscopy and phasor analysis," Science Advances, vol. 5, pp. 1-10, 2019.

Eom et al., "Synergistic combination of near-infrared irradiation and targeted gold nanoheaters for enhanced photothermal neural stimulation," Biomedical Optics Express, vol. 7, No. 4, pp. 1614-1625, 2016.

Farah et al., "Holographically patterned activation using photoabsorber induced neural-thermal stimulation," Journal of Neural Engineering, vol. 10, pp. 1-11, 2013.

Fischer et al., "Invited Review Article: Pump-probe microscopy," Review of Scientific Instruments, vol. 87, pp. 1-22, 2016.

Fu et al., "Probing skin pigmentation changes with transient absorption imaging of eumelanin and pheomelanin," Journal of Biomedical Optics, Vo. 13, No. 5, pp. 1-7, 2008.

Gilbert et al., "Controlling Brain Cells with Light: Ethical Considerations for Optogenetic Clinical Trials," AJOB Neuroscience, vol. 5, No. 3, pp. 3-11, 2014.

Guo et al., "Long-range hot-carrier transport in hybrid perovskites visualized by ultrafast microscopy," Science, vol. 356, pp. 59-62, 2017.

Hallett, "Transcranial magnetic stimulation and the human brain," Nature, vol. 406, pp. 147-150, 2000.

Hamblin et al., "Shining light on the head: Photobiomodulation for brain disorders," BBA Clinical, vol. 6., pp. 113-124, 2016.

Henderson et al., "Near-infrared photonic energy penetration: can infrared phototherapy effectively reach the human brain?" Neuropsychiatric Disease and Treatment, vol. 11, pp. 2191-2208, 2015.

Huang et al., "High-Speed Spectroscopic Transient Absorption Imaging of Defects in Graphene," Nano Letters, vol. 18, pp. 1489-1497, 2018.

Huang et al., "Ultrafast Transient Absorption Microscopy Studies of Carrier Dynamics in Epitaxial Graphene," Nano etters, vol. 10, pp. 1308-1313, 2010.

Jain et al., "Calculated Absorption and Scattering Properties of Gold Nanoparticles of Different Size, Shape, and Composition: Applications in Biological Imaging and Biomedicine," J. Phys. Chem. B, vol. 110, pp. 7238-7248, 2006.

Jiang et al., "Metabolizable Semiconducting Polymer Nanoparticles for Second Near-Infrared Photoacoustic Imaging," Advanced Materials, vol. 31, pp. 1-9, 2019.

Jiang et al., "Optoacoustic brain stimulation at s ubmillimeter spatial precision," Nature Communications, vol. 11, No. 881, pp. 1-9, 2020.

Jones et al., "Fluorescence Microplate-Based Assay for Tumor Necrosis Factor Activity Using SYTOX Green Stain," Analytical Biochemistry, vol. 293, pp. 8-15, 2001.

Jung et al., "Fast Detection of the Metallic State of Individual Single-Walled Carbon Nanotubes Using a Transient-Absorption Optical Microscope," Physical Review Letters, vol. 105, pp. 1-4, 2010.

Kamimura et al., "Ultrasound Neuromodulation: Mechanisms and the Potential of Multimodal Stimulation for Neuronal Function Assessment," Frontiers in Physics, vol. 8, Art. 150, pp. 1-9, 2020.

Kang et al., "C. elegans TRP Family Protein TRP-4 Is a Pore-Forming Subunit of a Native Mechanotransduction Channel," Neuron, vol. 67, pp. 381-391, 2010.

"Kanju et al., ""Pleiotropic function of TRPV4 ion channels in the centralnervous system,"" Experimental Physiology, vol. 101, pp. 1472-1476, 2016."

Koirala et al., "Inverse design of long-range intensity correlation in scattering media," Phys. Rev. B, vol. 100, pp. 1-9, 2019.

Krasovitski et al., "Intramembrane cavitation as a unifying mechanism for ultrasound-induced bioeffects," Proceedings of the National Academy of Sciences of the United States of America, vol. 108, No. 8, pp. 3258-3263, 2011.

Kubanek et al., "Ultrasound Elicits Behavioral Responses through Mechanical Effects on Neurons and Ion Channels In a Simple Nervous System," The Journal of Neuroscience, vol. 38, No. 12, pp. 3081-3091, 2018.

Kubanek et al., "Ultrasound modulates ion channel currents," Scientific Reports, vol. 6, No. 24170, pp. 1-14, 2016.

Lee et al., "Gold nanostar-mediated neural activity control using plasmonic photothermal effects," Biomaterials, vol. 153, pp. 59-69, 2018.

"Lee et al., ""Thermo-plasmonic gold nanofilms for simple andmass-producible photothermal neural interfaces,"" Nanoscale, vol. 10, pp. 9226-9235, 2018."

Legon et al., "Pulsed Ultrasound Differentially Stimulates Somatosensory Circuits in Humans as Indicated by EEG and fMRI," PLoS One, vol. 7, No. 12, pp. 1-14, 2012.

* cited by examiner

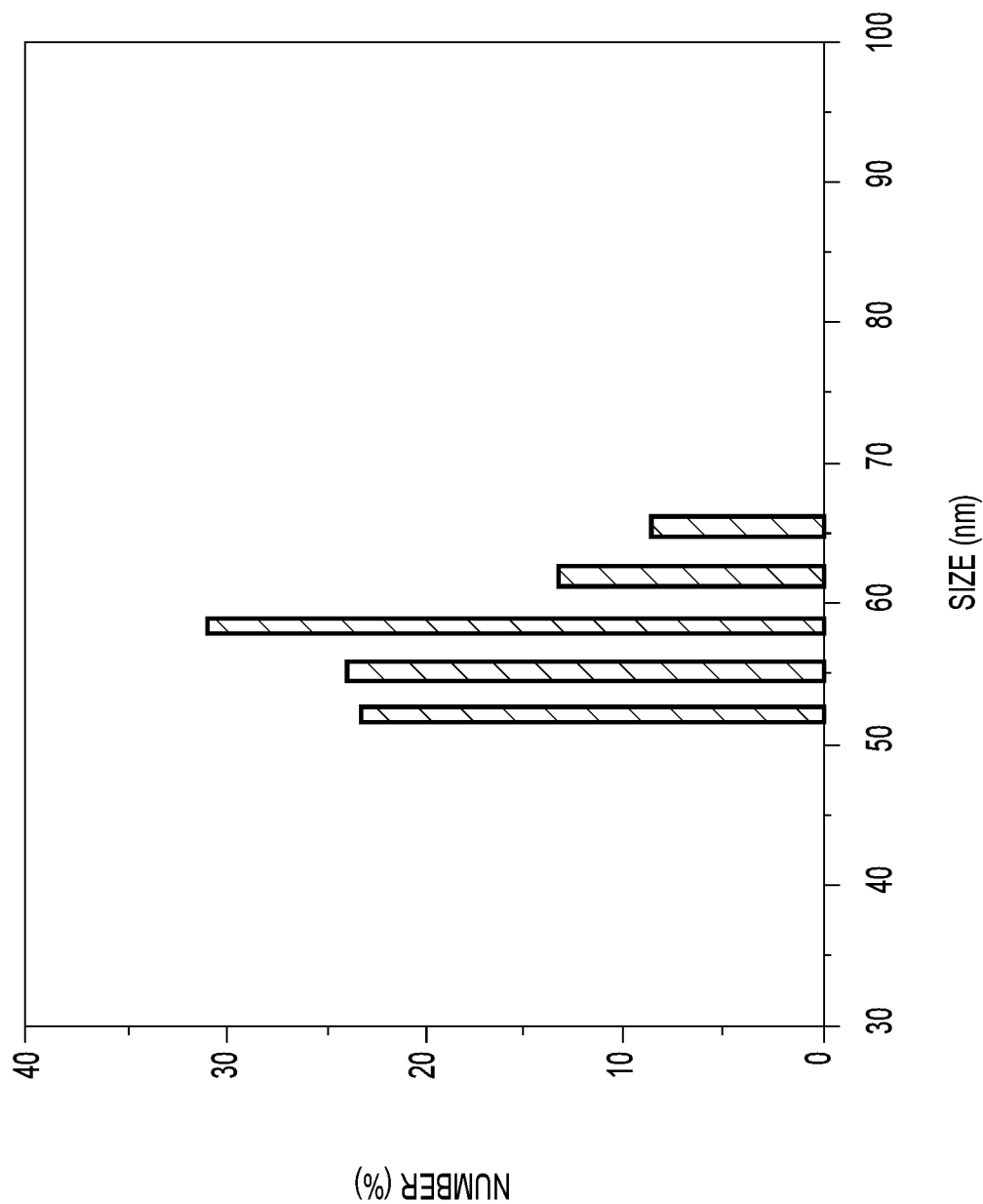

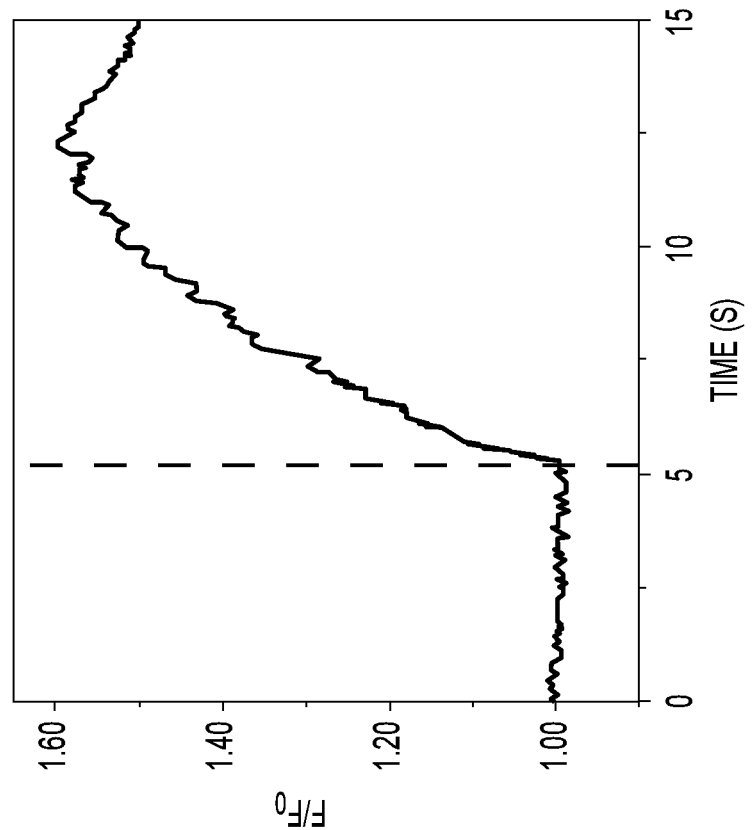
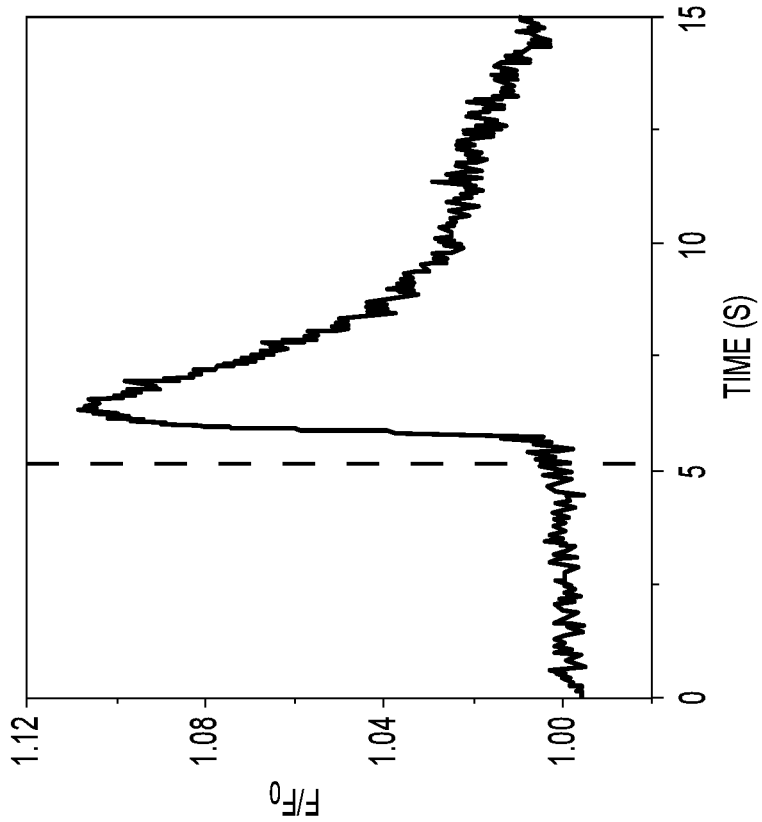

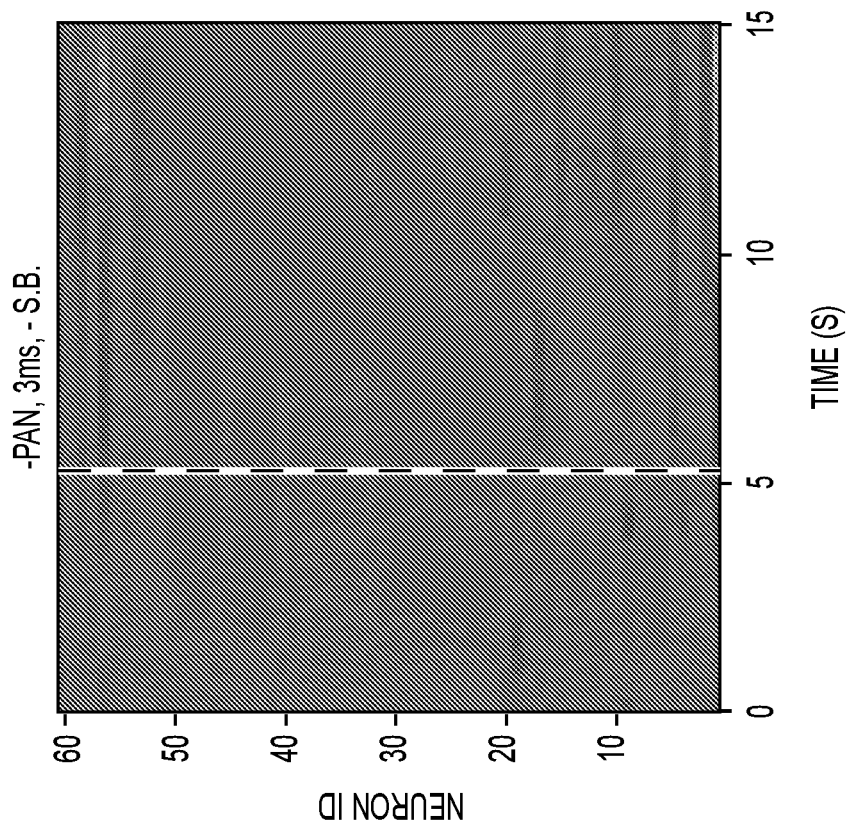
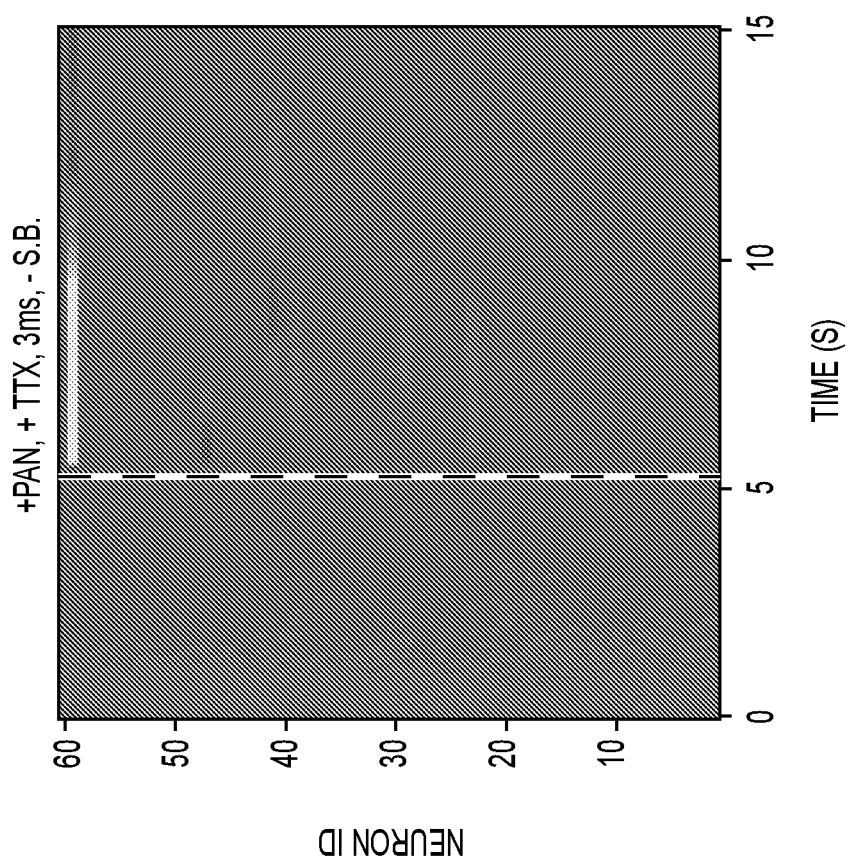

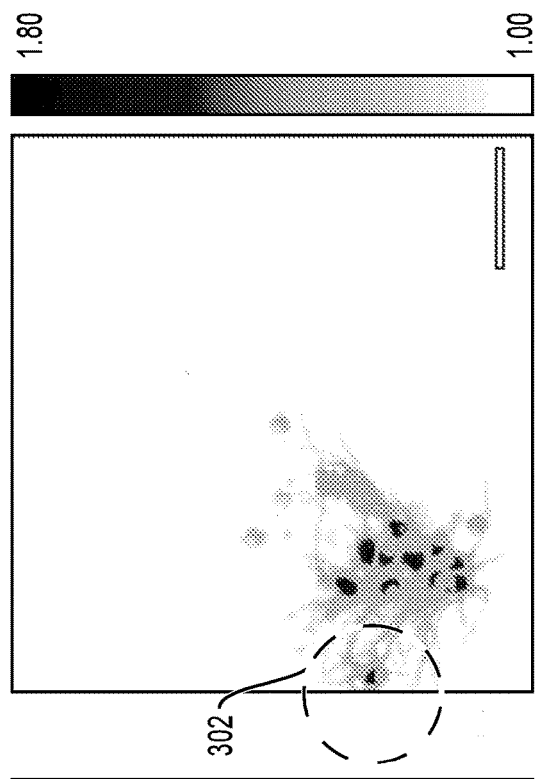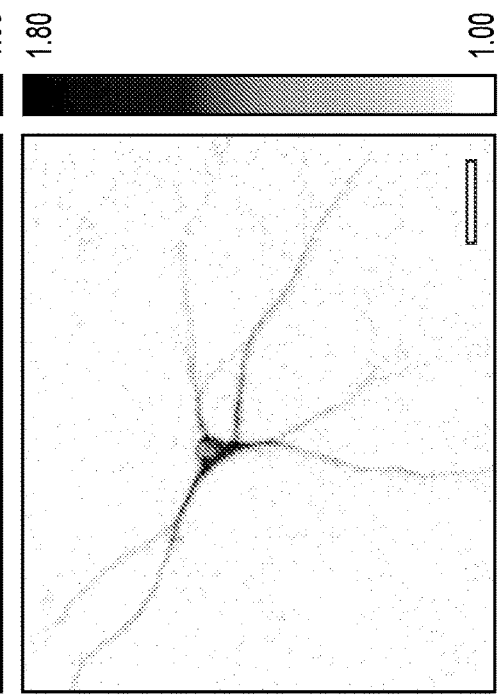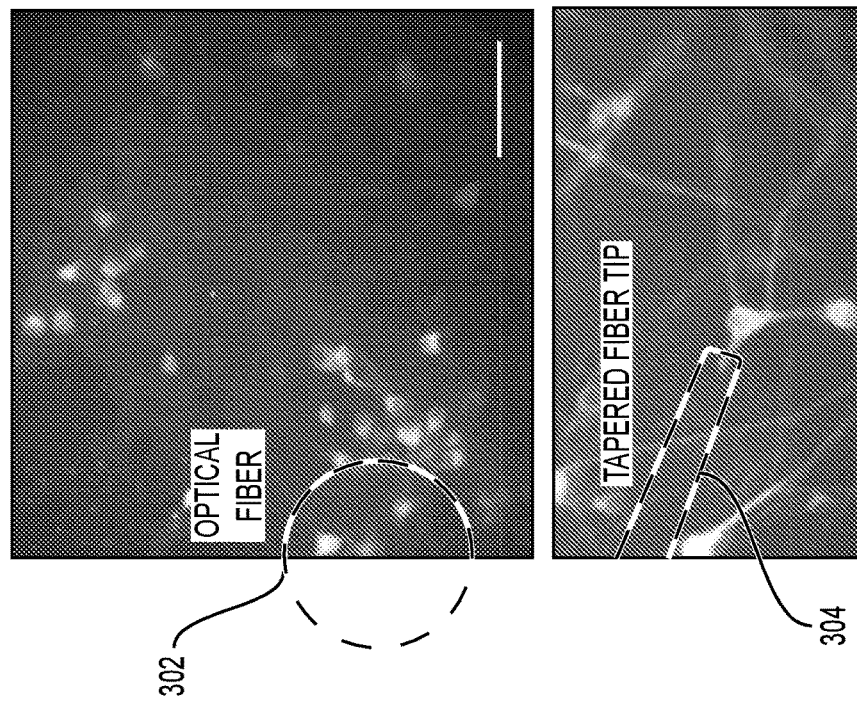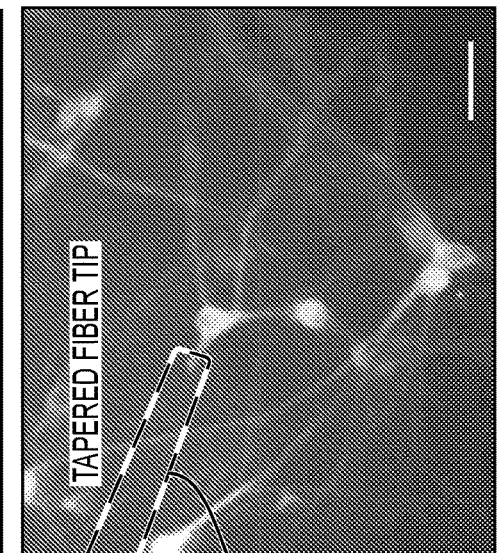
FIG. 3A
FIG. 3B
FIG. 3C
FIG. 3D

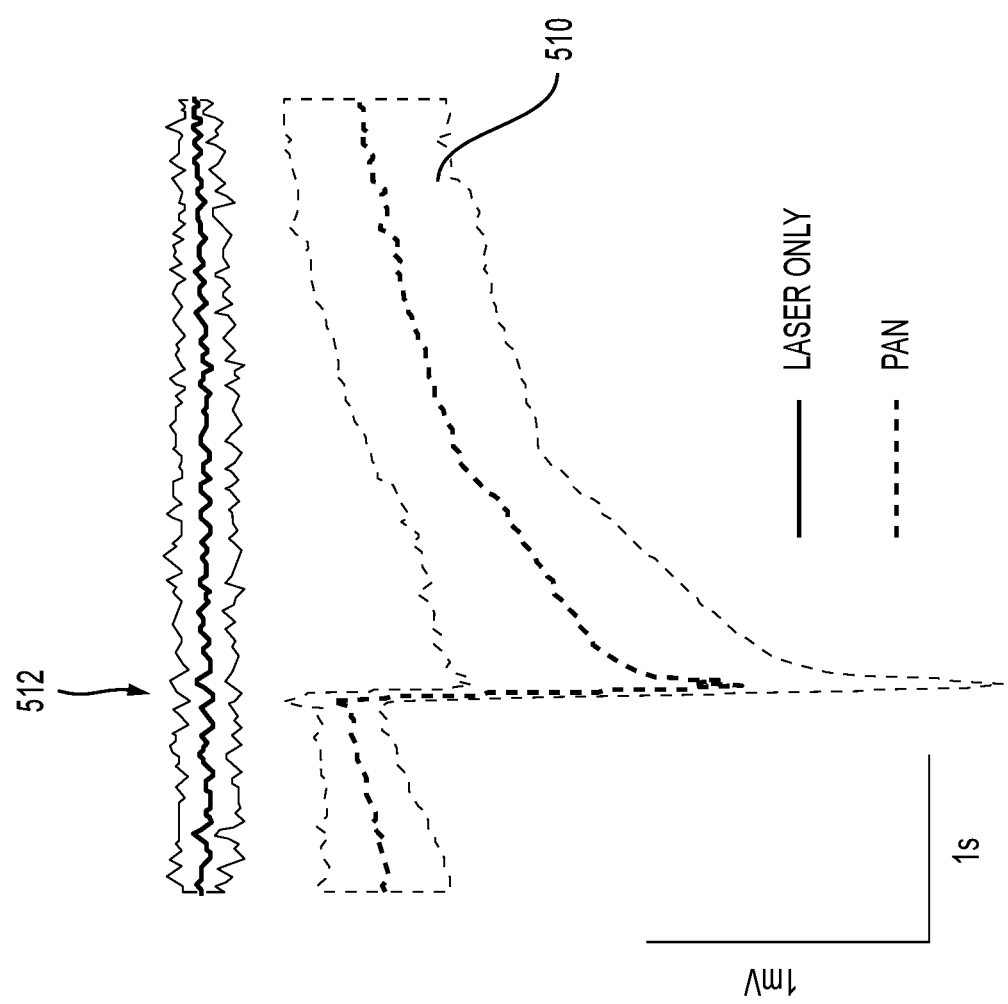

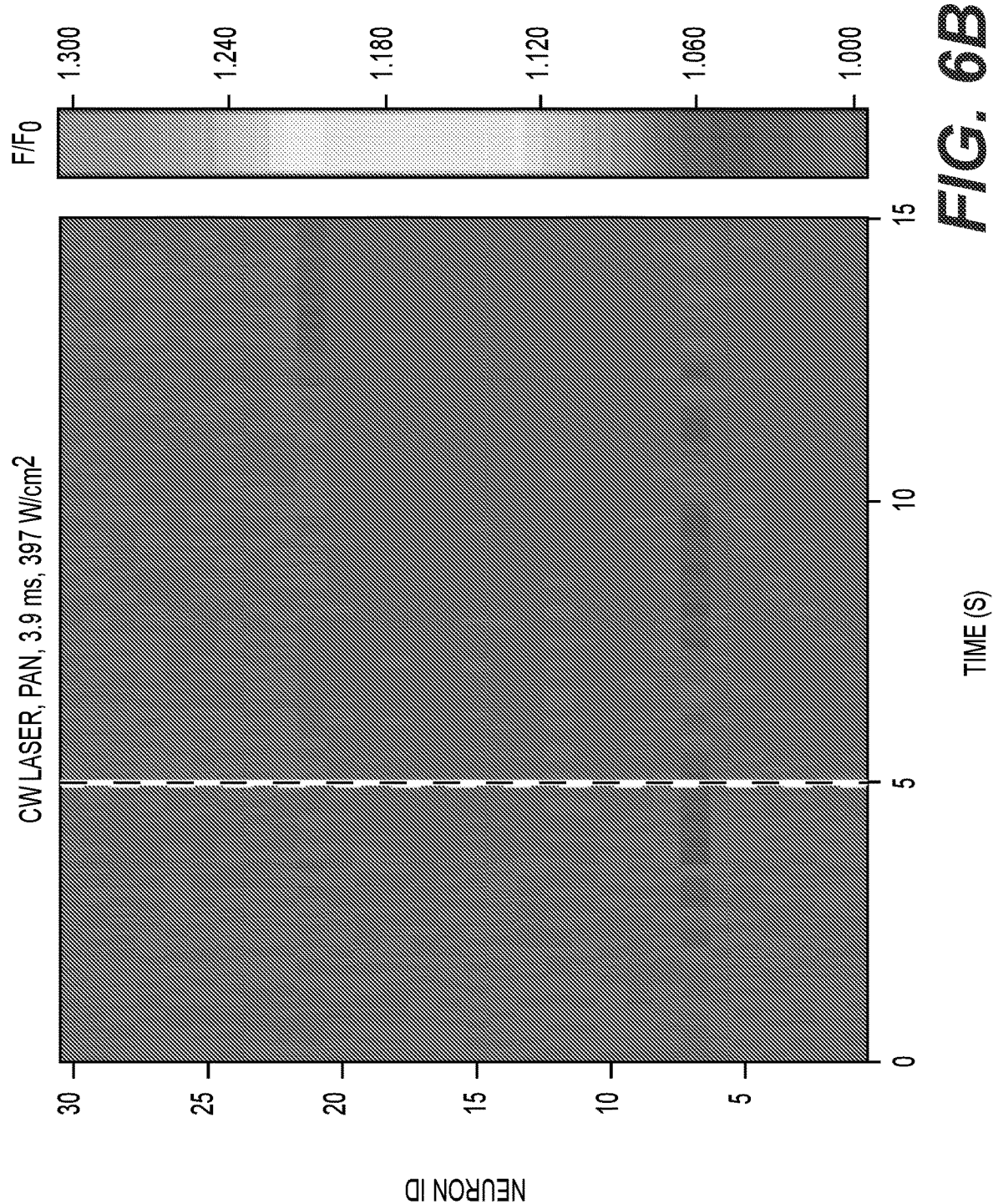

NEURAL STIMULATION IN VITRO AND IN VIVO BY PHOTOACOUSTIC NANOTRANSDUCERS

RELATED APPLICATIONS

This application claims priority to U.S. provisional application No. 63/305,863 filed on Feb. 2, 2022, the contents of which is included herein in its entirety.

GOVERNMENT SUPPORT

This invention was made with government support under NS109794 awarded by the National Institutes of Health. The government has certain rights in the invention.

BACKGROUND

Neural stimulation is an important tool enabling our understanding of how brains function and treatments of neurological disorders. Electrical stimulation is the basis of current implantable devices and has already used in the clinical treatment of depression, Parkinson's, and Alzheimer's diseases. These devices, often made of metal electrodes, are limited by their invasive nature, inability to targeting precisely due to current spread, and its magnetic resonance imaging (MRI) incompatibility. Noninvasive clinical or pre-clinical methods, such as transcranial magnetic stimulation (TMS) and transcranial direct current stimulation (tDCS) do not require a surgical procedure but offer a spatial resolution on the order of several millimeters.

Optogenetics has been shown as a powerful method modulating population neural activities in rodents more precisely and with cell specificity. It requires genetic modification through viral infection, which makes it challenging to be applied to humans. Ultrasound neuromodulation as an emerging noninvasive neuromodulation method has been demonstrated to evoke action potentials in vitro, and behavioral responses in vivo in rodents, nonhuman primates and even in human subjects. However, the spatial resolution for conventional ultrasound neuromodulation is still limited to several millimeters. More recently, a fiber based optoacoustic converter has been proposed and demonstrated to achieve neuromodulation with submillimeter spatial resolution utilizing the optoacoustic effect, yet it requires surgical implantation for in vivo applications.

Nanostructures target neuron membrane locally, convert and amplify the external excitation to local stimuli, offering new interfaces as promising alternative neural stimulation approaches. Gold nanoparticles and nanorods were studied for photothermal neural stimulation in vitro. Gold nanoparticles and carbon nanotubes were also used for photothermal-driven optocapacitive stimulation in vitro. Photoelectrical stimulations may be performed with silicon nanostructures. In these light driven stimulations, the wavelengths used were mostly in the range of 520-808 nm, which has limited penetration through skulls and in brain tissue. To offer deeper penetration, thermal stimulation triggered by nanoparticles absorbing longer-wavelength light or magnetic field has also been investigated. Photothermal neural stimulation is performed in vitro using bioconjugated polymer nanoparticles absorbing 808 nm and binding to transient receptor potential cation channel subfamily V member 1 (TRPV1). Gene transfections are used to over-express the thermal sensitive ion channels TRPV1 and then utilized the magneto-thermal effect of the paramagnetic nanoparticles to activate these channels. In these studies, significant local temperature rise, exceeding the thermal threshold of the ion channels, e.g., 43° C. in the case of TRPV 1, for a period longer than several second, was observed, thus raising concerns over safety of thermally activated neural stimulation. The magneto-electric nanoparticles are used under an applied magnetic field to perturb the voltage-sensitive ion channels for neuron modulation. Notably, these magnetic stimuli-based techniques deliver a spatial precision relying on the confinement of the magnetic field, which is on the millimeter to centimeter scale. New technologies and concepts are still sought to achieve noninvasive, genetic free and precise neural stimulation.

SUMMARY

An example photoacoustic system for neurostimulation includes a light producing device for producing light of a specific wavelength. At least one nanotransducer is binded on a surface of a neuron. The nanotransducer converts the light with the specific wavelength into at least one acoustic wave at or near the neuron.

The specific wavelength may be between 800 nm and 1800 nm. The light may be a light pulse. The light producing device may be coupled to a tapered fiber for delivery of the light. The at least one nanotransducer may include semiconducting polymer nanoparticles. The at least one nanotransducer may be photoacoustic nanotransducers (PANs) for neural stimulation. The at least one nanotransducer may be implemented in vitro on the neuron. The at least one nanotransducer may be implemented in vivo on the neuron. The at least one nanotransducer may be injected thru blood to reach the neuron. The at least one nanotransducer may be positioned on the neuron via openings of the blood-brain barrier. The at least one nanotransducer may include negligible cumulative heat effects.

An example method for neurostimulation includes producing light of specific wavelength and positioning at least one nanotransducer binded on a surface of a neuron. Moreover, the method includes converting, using the nanotransducer, the light with the specific wavelength into at least one acoustic wave at or near the neuron.

The specific wavelength may be between 800 nm and 1800 nm. The light may be a light pulse. The step of producing the light may include coupling the light producing device to a tapered fiber for delivery of the light. The at least one nanotransducer may include semiconducting polymer nanoparticles. The at least one nanotransducer may be a plurality of photoacoustic nanotransducers (PANs) for neural stimulation. The method may further include implementing the at least one nanotransducer in vitro on the neuron. The method may further include implementing the at least one nanotransducer in vivo on the neuron. The method may further include injecting the at least one nanotransducer thru blood to reach the neuron. The method may further include positioning the at least one nanotransducer on the neuron via openings of the blood-brain barrier. The at least one nanotransducer may include negligible cumulative heat effects.

An example system for neurostimulation includes a light producing device producing light of specific wavelength. At least one nanotransducer is binded on a surface of a neuronal membrane and targeting at least one mechanosensitive ion channel. The nanotransducer convers the light with the specific wavelength into at least one acoustic wave perturbing the at least one mechanosensitive ion channel directly.

The specific wavelength may be between 800 nm and 1800 nm. The light may be a light pulse. The light producing device may be coupled to a tapered fiber for delivery of the light. The at least one nanotransducer may be a plurality of photoacoustic nanotransducers (PANs) for neural stimulation. The at least one nanotransducer may be injected thru blood to reach the neuron. The at least one nanotransducer may be positioned on the neuron via openings of the blood-brain barrier. The at least one nanotransducer may include negligible cumulative heat effects.

Additional features and advantages of the present disclosure is described in, and will be apparent from, the detailed description of this disclosure.

BRIEF DESCRIPTION OF THE DRAWINGS

The disclosure is illustrated by way of example, and not by way of limitation, in the figures of the accompanying drawings in which like reference numerals are used to refer to similar elements. It is emphasized that various features may not be drawn to scale and the dimensions of various features may be arbitrarily increased or reduced for clarity of discussion.

FIGS. 1A-1K illustrate surface modified PANs sufficiently binding to neurons and corresponding results.

FIGS. 2A-2H illustrate PANs induced neural stimulation and corresponding results.

FIGS. 3A-3D illustrate the spatial distribution of neuron activation induced by PAN.

FIGS. 5A-5D illustrate in vivo neural stimulation by injected PANs and corresponding results.

FIGS. 6A-6F illustrate PAN-mediated neural stimulation not thermally induced.

DETAILED DESCRIPTION

Figure 1A:
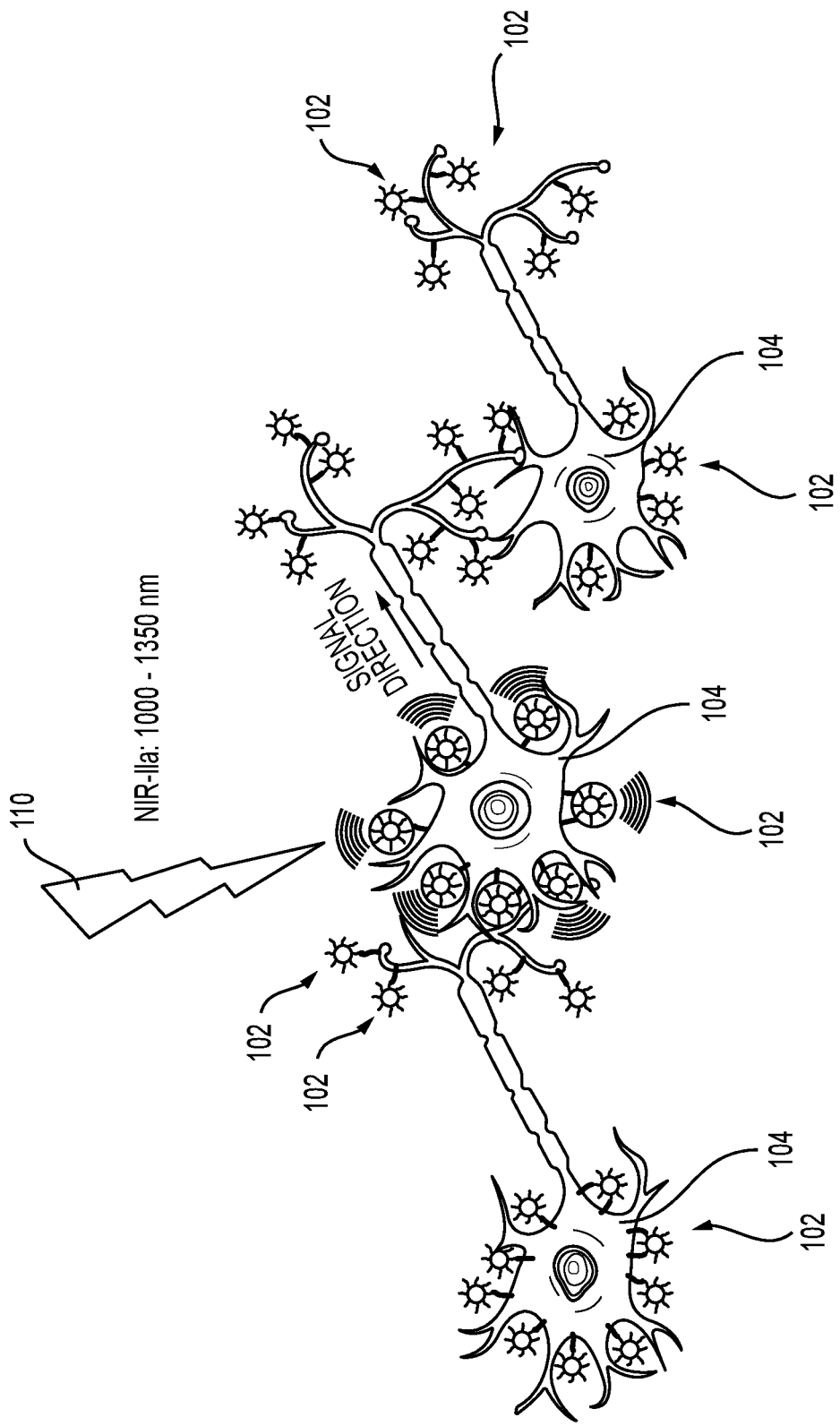

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may recognize that other elements and/or operations may be desirable and/or necessary to implement the devices, systems, and methods described herein. But because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

The terminology used herein is for the purpose of describing particular example embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. That is, terms such as "first," "second," and other numerical terms, when used herein, do not imply a sequence or order unless clearly indicated by the context.

This disclosure describes a method and system for in vitro and in vivo neural stimulation using semiconducting polymer nanoparticles based photoacoustic nanotransducers (PANs). The PANs strongly absorb the nanosecond pulsed laser in the near-infrared second window (NIR-II) and generate localized acoustic waves. PANs are shown to be surface-modified and selectively bind onto neurons. PAN-mediated activation of primary neurons in vitro is achieved with ten 3-nanosecond laser pulses at 1030 nm over a 3-millisecond duration. In vivo neural modulation of mouse brain activities and motor activities is demonstrated by PANs directly injected into brain cortex. With sub-millimeter spatial resolution and negligible heat deposition, PAN stimulation is a new non-genetic method for precise control of neuronal activities, opening potentials in non-invasive brain modulation.

The premise for using this approach is based on the unparalleled advantages provided by our tailor-designed PAN: (1) Strongly and uniquely absorbing light in the near-infrared second window (NIR-II, 1000 to 1700 nm). Such wavelength has the capability of penetrating human skull, offering the potential of non-surgical brain stimulation through light excitation; (2) Providing highly efficient conversion of optical energy to mechanic energy, in the form of ultrasound waves, with minimal photo-thermal energy conversion in tissue to assure biosafety; (3) Designed to be <60 nm and bound to neural membrane, therefore the spatial resolution of the proposed stimulation is defined by the focus size of light, potentially at optical diffraction limit (~500 nm) for single-cell stimulation in vitro, and at the level of ~100 micron in brain considering tissue scattering. Such spatial resolution is 4 orders of magnitude in vitro and 1 to 2 orders of magnitude in vivo better than current low-frequency ultrasound (~5 mm). (4) With diameters less than 60 nm it can be delivered non-surgically into brain through combining intravenous (IV) injection and ultrasound-mediated transient opening of blood brain barrier (BBB).

Figure 1B:
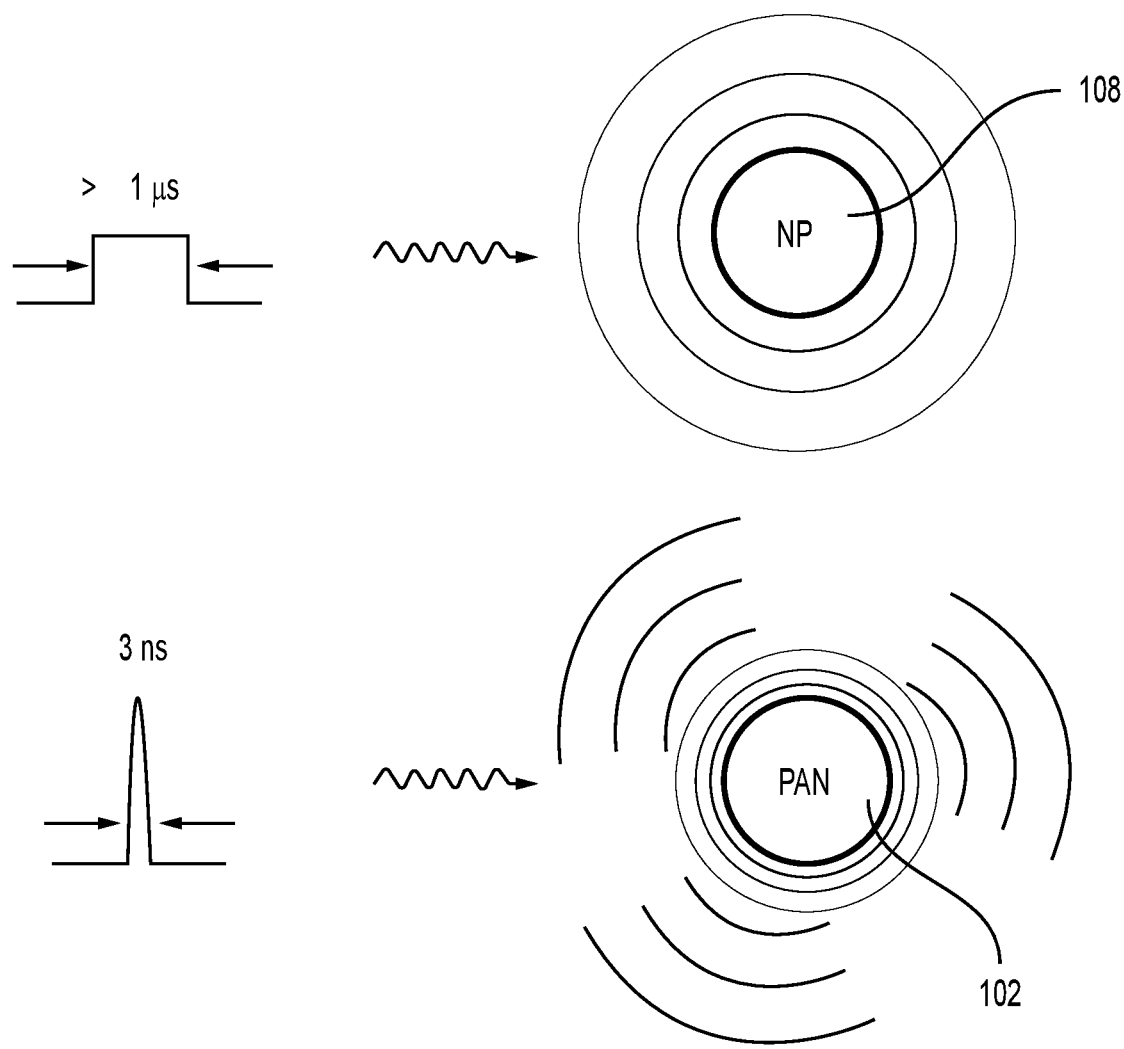

FIGS. 1A-1K illustrate surface modified PANs sufficiently binding to neurons and corresponding results. The development and application of photoacoustic nanotransducers (PANs) 102 enable non-genetic neural stimulation in cultured primary neurons 104 and in mouse brain in vivo, as shown in FIG. 1A. A PAN 102, based on synthesized semiconducting polymer nanoparticles, may efficiently generate localized ultrasound by a photoacoustic process upon absorption of nanosecond (3 ns) pulsed light 110 in the NIR-II window (1000 nm to 1700 nm) compared to a standard nanoparticle 108, as shown in FIG. 1B. The NIR-II light 110 has the capability of centimeter-deep tissue penetration, which is beyond the reach of visible light currently used in optogenetics. The surface of each PAN 102 may be modified for non-specific binding to neuronal membrane 104 and specific targeting of mechanosensitive ion channels, respectively.

Upon excitation at 1030 nm, PANs 102 on the neuronal membrane 104 may successfully activate rat cortical neurons, confirmed by real time fluorescence imaging of GCaMP6f. The spatial resolution of the PAN stimulation was shown to be completely determined by the illumination area of the light and single neuron stimulation was demonstrated under excitation of NIR-II light delivered by a tapered fiber. In vivo motor cortex activation and invoked subsequent motor responses are demonstrated through PANs 102 directly injected into a mouse living brain. Importantly, the heat generated by the nanosecond laser pulses is confined inside the PAN, resulting in a transient temperature rise during the photoacoustic process, evident by finite element modeling simulations. Collectively, the finding shows photoacoustic nanotransducers may be a platform for modulating neuronal activities. It is triggered by NIR-II light and shows neglectable temperature increase, opening up opportunities for deep-penetrated-light controlled neural activation with high precision.

Figure 1C:
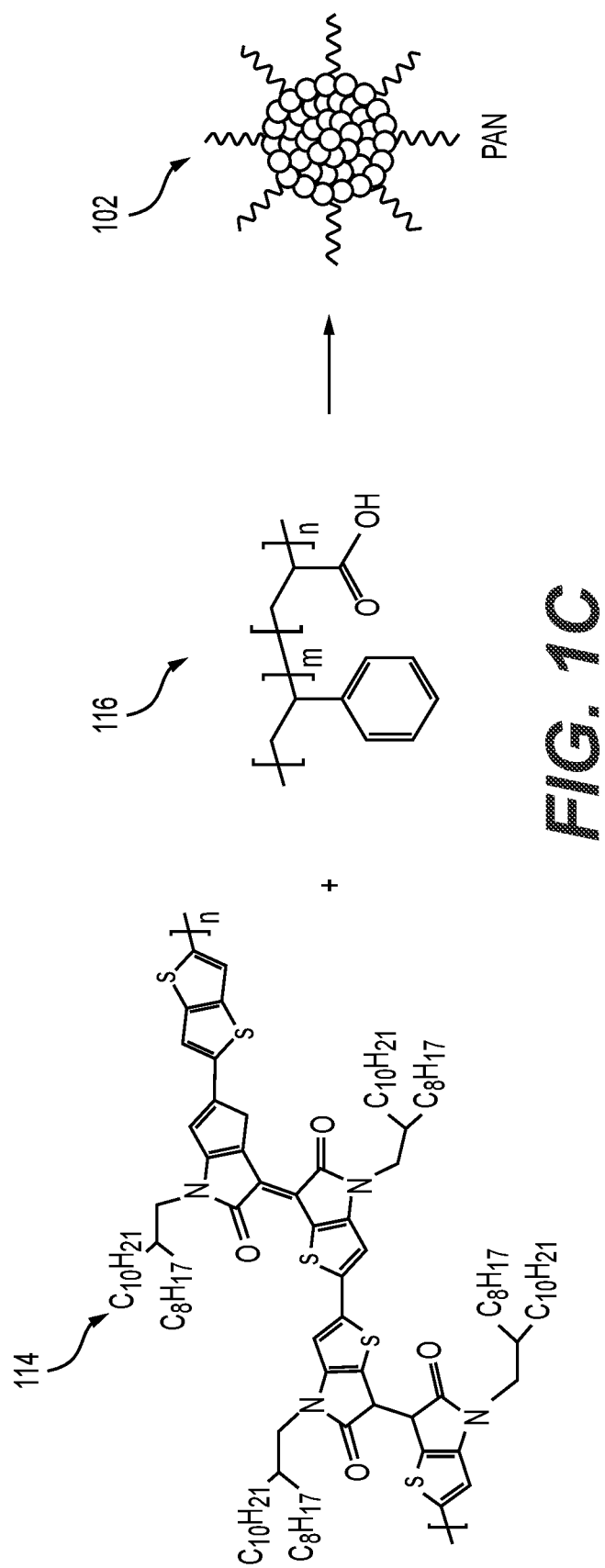
Figure 1E:
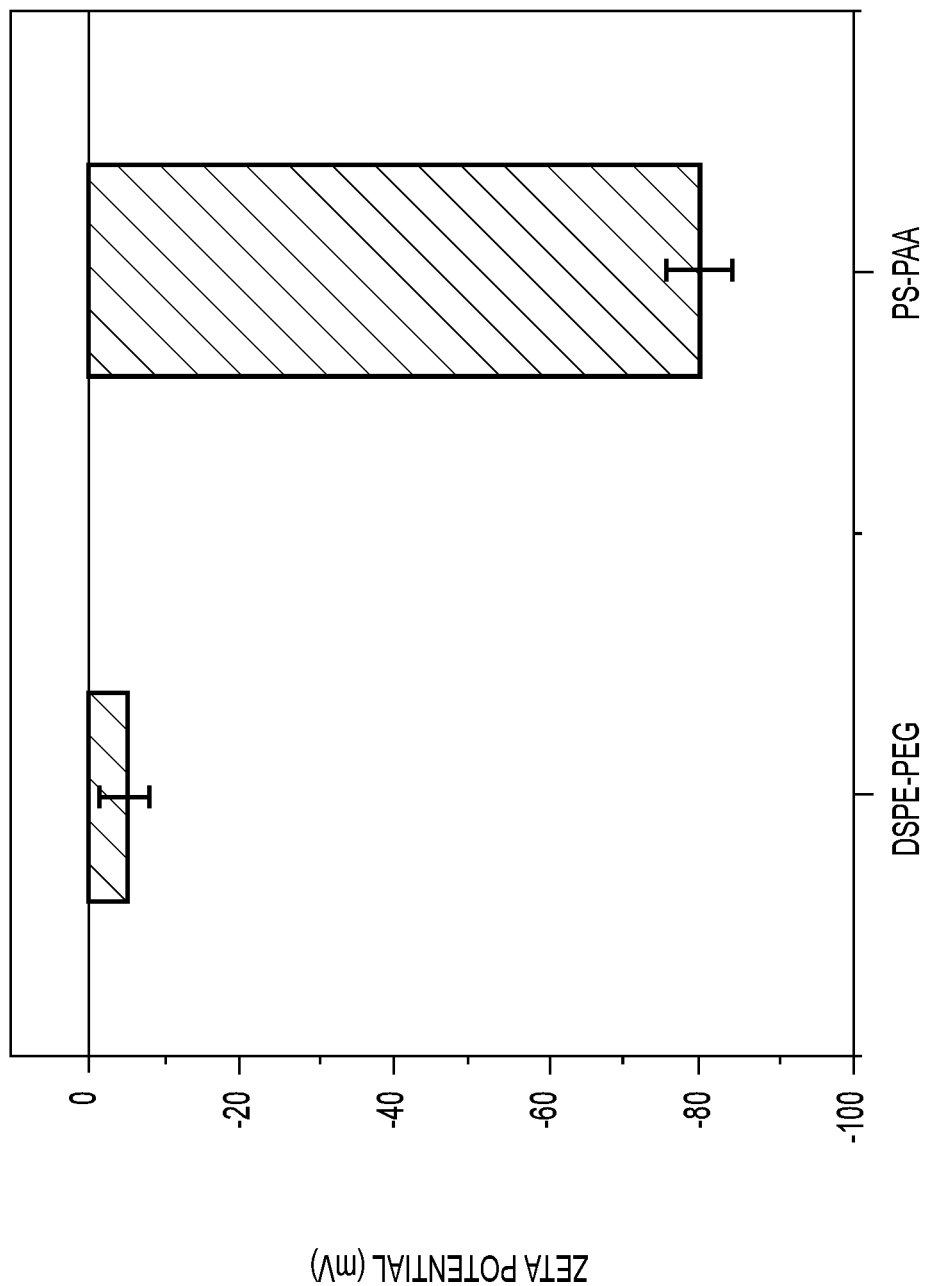

A NIR-II absorbing semiconducting polymer bis-isoindigo-based polymer (BTII) 114 is first synthesized. To obtain nanoparticles, the polymer may be modified with polystyrene-block-poly(acryl acid) (PS-b-PAA) 116 via a nanoprecipitation method, as shown in FIG. 1C. The PS-b-PAA 116 was chosen due to the amphiphilic nature of its chemical structure. The hydrophobic polystyrene portion forms a π-π stacking with the polymer, while the hydrophilic poly(acryl acid) (PAA) makes the polymer into water-soluble nanoparticles with carboxyl groups decorated on the surface. FT-IR spectrum confirmed the presence of carboxyl groups, indicating the successful modification. The PANs were dispersed in aqueous solution for characterization. The size of nanoparticles prepared was measured to be 58.0±5.2 nm using dynamic light scattering (DLS), as shown in FIG. 1D. Transmission electron microscopy imaging of PAN shows an average particle diameter of 52.9±12.2 nm, consistent with the DLS measurement results, The nanoparticles were found to be negatively charged indicated by a potential of −79.79±4.04 mV through the zeta potential measurement. To confirm the surface negative charge is introduced by the surfactant PS-b-PAA, surface modification was performed using 1,2-distearoyl-sn-glycero-3-phosphoethanolamine-N-[(polyethylene glycol)-2000] (DSPE-PEG), a neutrally charged surfactant, as a comparison. DSPE-PEG modified PANs were found to be charged with −4.88±3.06 mV, as shown in FIG. 1E.

Figure 1F:
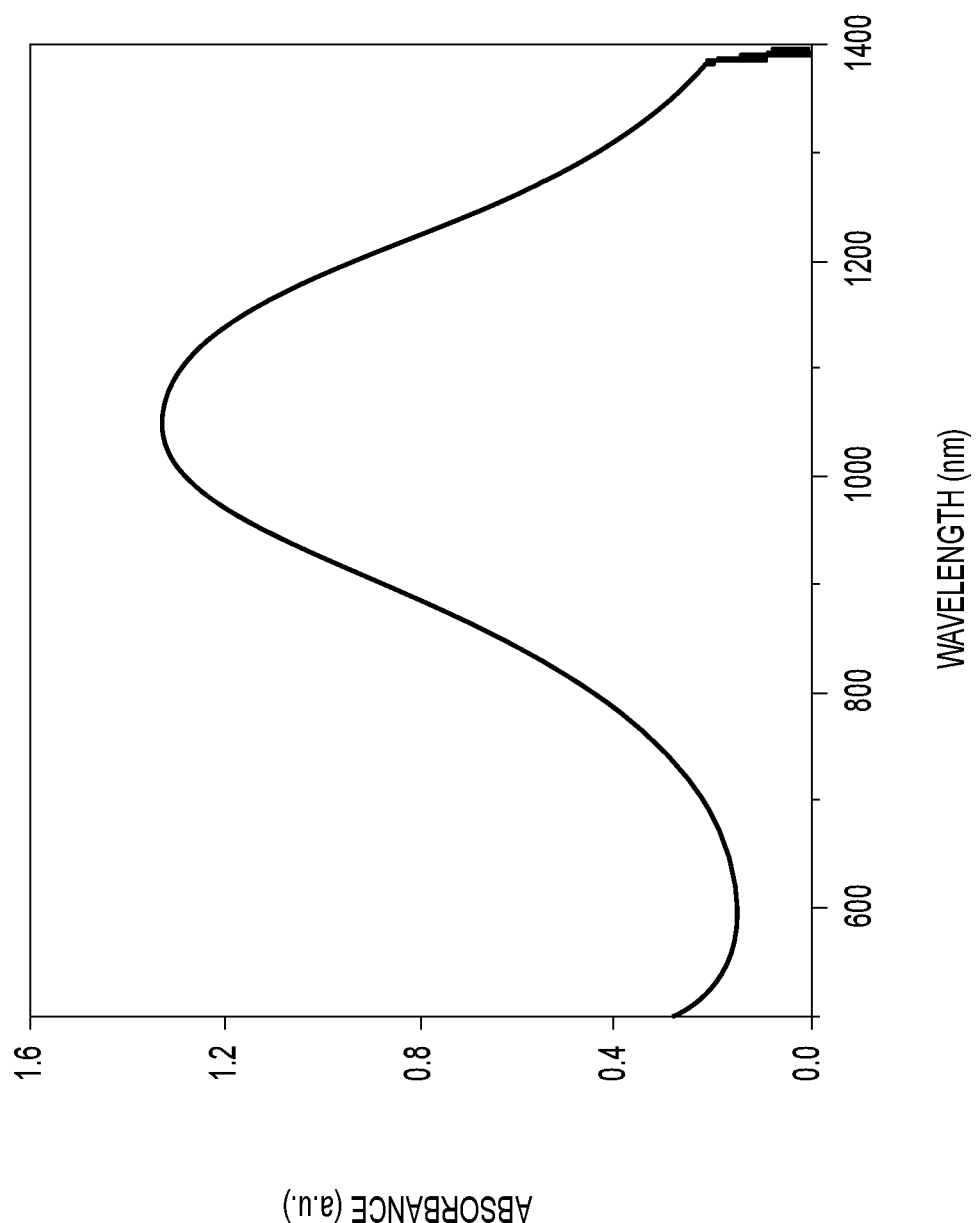

The planar backbone of the semiconducting polymer chain pushed the absorption to the NIR-II window. This was confirmed by Ultraviolet (UV)-Visible-NIR spectroscopy. FIG. 1F shows the nanoparticles absorb broadly NIR-II light from 800 to 1800 nm with a peak at 1100 nm. Next, it was tested whether PAN can generate sufficient optoacoustic wave. In the optoacoustic process, optoacoustic wave is generated following a transient temperature increase and thermal expansion of the nanoparticle. Importantly, two conditions, i.e., stress confinement and thermal confinement, need to be met for efficient photoacoustic generation. The initial pressure $p_0$ generated is related to light absorption by the following expression: $p_0 = \Gamma \mu_a F$, where $\mu_a$ is the absorption coefficient of the absorber, F is the local light fluence, and $\Gamma$ is the Grüneisen parameter. The Grüneisen parameter can be expressed as $\Gamma = \beta v_s^2 / C_p = \beta / (\kappa \rho C_p)$, where $\beta$ is the isobaric volume expansion coefficient, $C_p$ is the heat, $v_s$ is the acoustic speed, $\kappa$ is the isothermal compressibility, and $\rho$ is the mass density. Per the stress confinement, to build up the thermoelastic pressure within a nanoparticle with a diameter less than 100 nm nanoparticles, considering the speed of sound, a laser pulsed less than 67 picosecond is required. Yet, a mode-locked picosecond pulsed laser usually has several orders of magnitude lower pulse energy than a Q-switched nanosecond pulsed laser. Therefore, nanosecond pulsed lasers are widely used for photoacoustic applications. Regarding the thermal confinement, the thermal conduction time must be longer than the laser excitation pulse width to generate photoacoustic wave efficiently. The thermal conduction time can be approximated by $\tau_{th} = L^2/4D$, where L is the length of diffusion and D is the thermal diffusivity of local environment. In the case of PAN, the local environment is water around the cell body. Water has a thermal diffusivity of $1.4 \times 10^{-3}$ cm²/s, and the thermal diffusion length is approximated by the nano-particle size, which is ~60 nm. The thermal diffusion time constant $\tau_{th}$ is thus approximately 6 ns. Therefore, a nanosecond laser pulse of 3 ns was used to achieve the efficient photoacoustic generation.

Figure 1G:
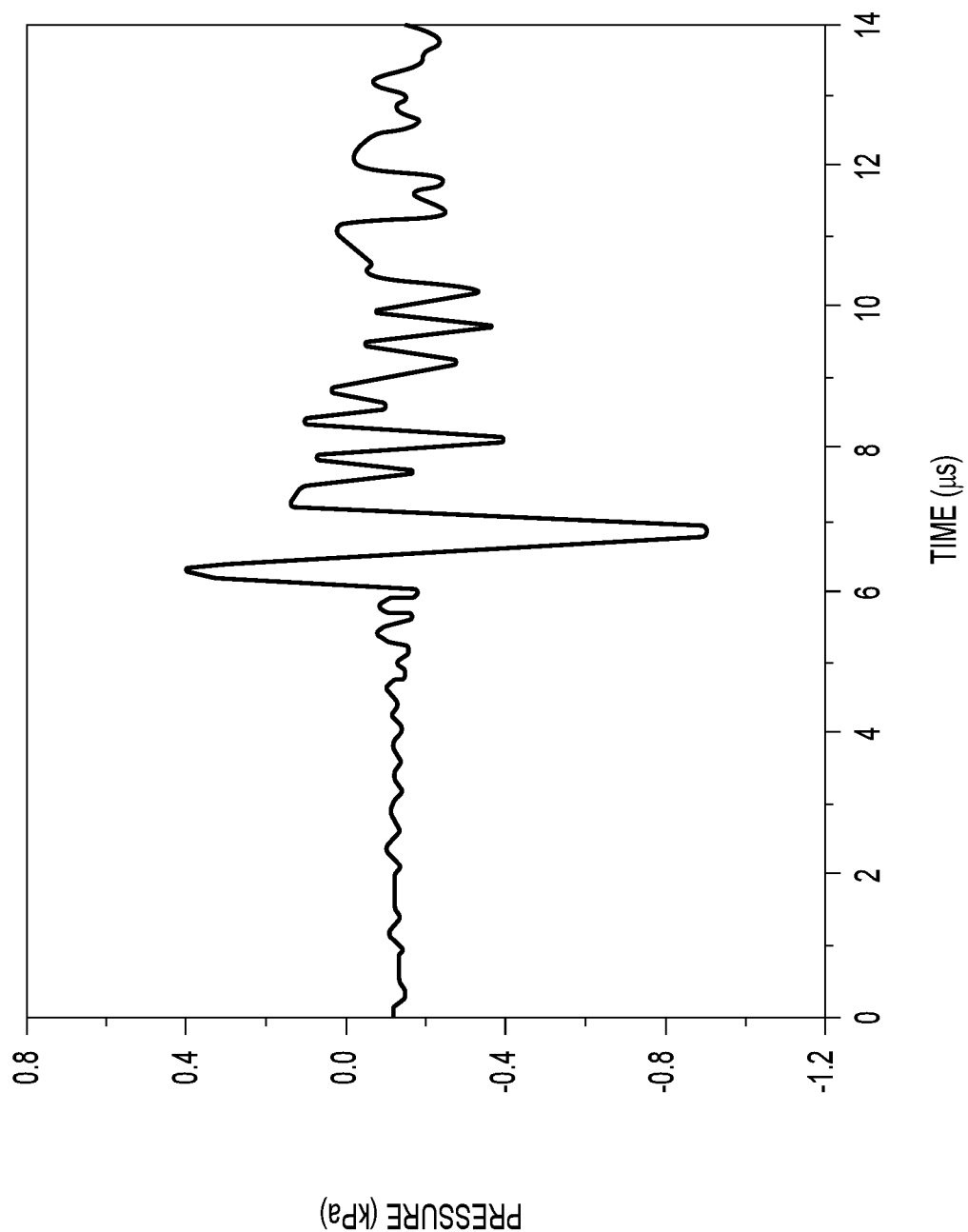

Measured with an ultrasound transducer with a central frequency at 5 MHz, 1.0 mg/mL nanoparticle solution exhibits a photoacoustic signal showing a waveform in time domain with approximately 2 μs in width and a peak to peak amplitude of 33.95 mV, as shown in FIG. 1G, under 1030 nm nanosecond laser with a pulse width of 3 ns, a repetition rate of 3.3 kHz, and an energy density of 21 mJ/cm². The peak pressure was measured to be 1.36 kPa using a needle hydrophone. Since these nanoparticles generate the strong photoacoustic signal under pulsed NIR-II light, they were termed PANs and studied their potential for neural binding and stimulation, as detailed below.

Nanoparticles with negatively charged surface can bind onto neuronal membrane, whereas positive and neutral nanostructures showed no interactions with neurons. To examine whether negatively charged PANs can bind onto the neuron membrane, PANs with embryonic cortical neurons are cultured and collected from Sprague Dawley (SD) rats. The neurons were first cultured for 15-18 days (Days in vitro, DIV15-18). A 150 μL 20 μg/mL PAN solution was added into the culture, reaching a concentration of 2 μg/m L. The same concentration was used in all experiments otherwise noted.

Confirming and quantifying the binding of PANs to neurons is critical for successful stimulation. Since the semiconducting polymer show strong intensive intrinsic transient absorption (TA) signals, a label free TA microscopy was used to visualize binding of PANs on neurons. In TA microscopy, two synchronized femtosecond laser pulse trains, pump, and probe respectively, are focused onto the sample. The electronically resonant pump laser pulse excites the molecule to its excited state, then the probe laser pulse probes the transient absorption change induced by the pump. Such nonlinear absorption signals are originated from the signature excited state dynamics of the molecule. With outstanding chemical specificity, TA microscopy has been applied to visualize molecular content in biological samples as well as characterization of nanomaterials, including semiconducting polymer nanoparticles.

Figure 1H:
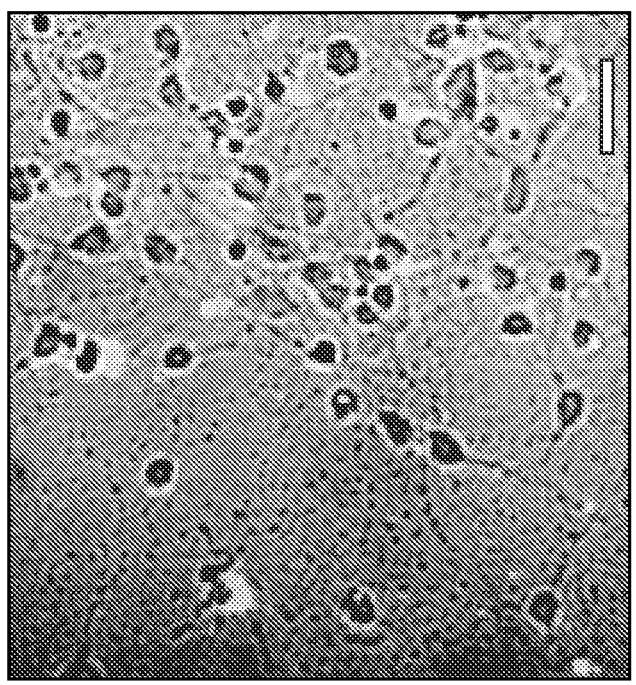

Specifically, a 200 fs laser pulses was used at 1045 nm and 845 nm as the pump and probe beams, respectively, with laser power fixed at 20 mW for both beams for TA imaging. To quantify the effective density of PANs bound to neurons, first the signal-to-noise ratio (SNR) of the TA signals of PAN solutions was measured with concentrations ranging from 2.0 to 55.0 μg/mL to obtain a TA calibration curve. The SNR of TA signals was found to be linear to the PAN concentration with a slope of 14.24 mL/μg. Next, neurons were incubated in culture supplemented with PANs for 15 minutes, rinsed three times with PBS to remove unbound PANs, and fixed the cells for TA imaging. The PANs were found to bind onto the neurons at an estimated density of 40.2±15.9 PANs per soma, as shown in FIG. 1H.

Figure 1I:
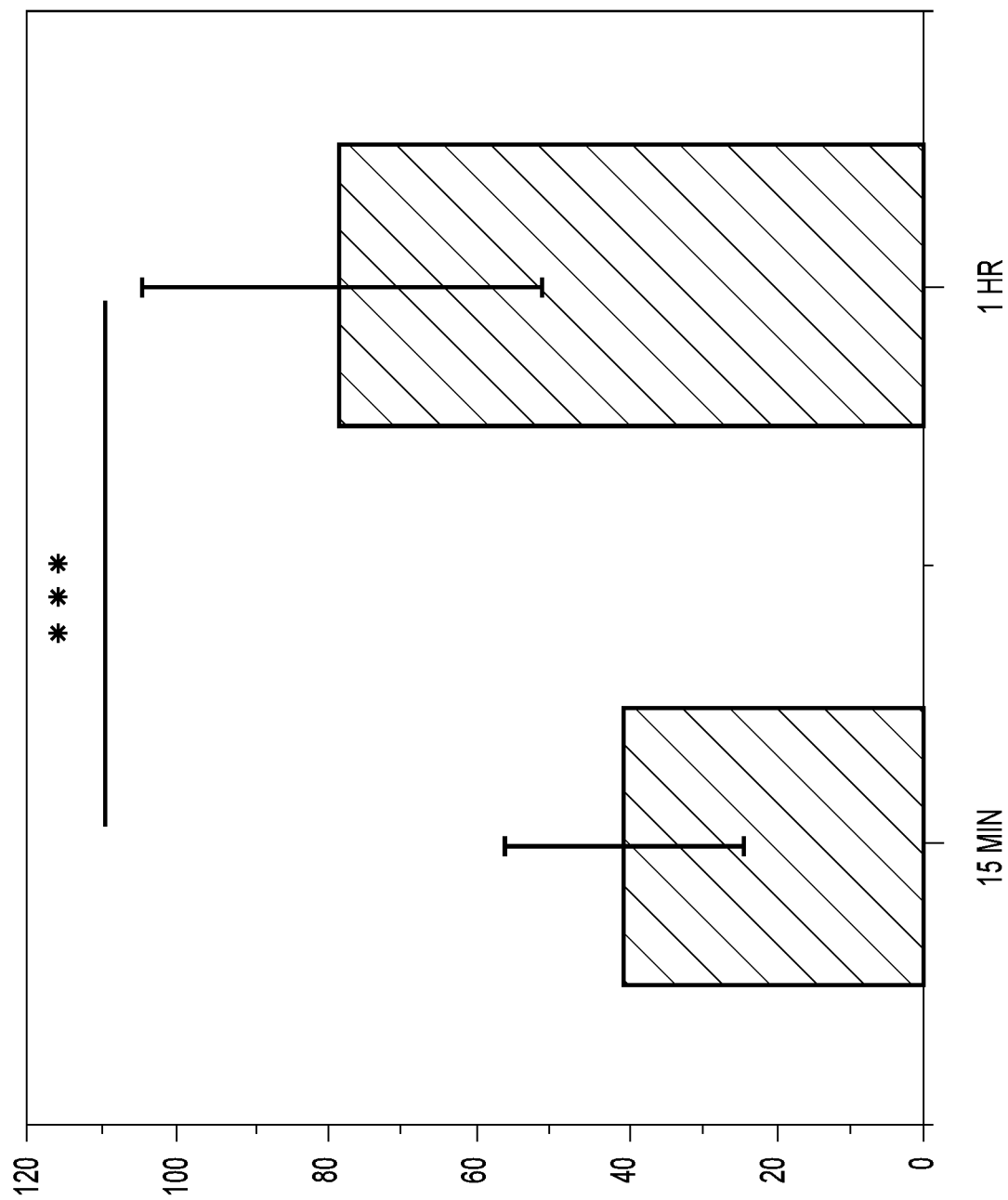

The number of PAN was calculated based on effective TA concentration estimated based on the measured TA intensity and the TA calibration curve, focused spot volume, and estimated molecular weight of PANs. Through depth resolved TA imaging, the PANs were found to bind mainly on the neuronal membrane instead of entering the neuron through endocytosis. By increasing the culture time to 1 hour, a higher binding density was achieved and the number of PANs per neuron on the soma area was found to be 78.1±26.7, as shown in FIG. 1I. In aqueous solution, the PAN prepared shows no aggregation. Based on the TA images of PAN co-cultured with neurons, some clusters of PANS were observed when binding to the membranes, possibly due to the complex cellular membrane environment. Different from TA image taken at 15 min co-culture, depth resolved TA imaging performed at 3 hours after PAN addition reveals strong TA signal from PAN located in the cytoplasm, which indicates endocytosis of PAN into the soma.

Figure 1J:
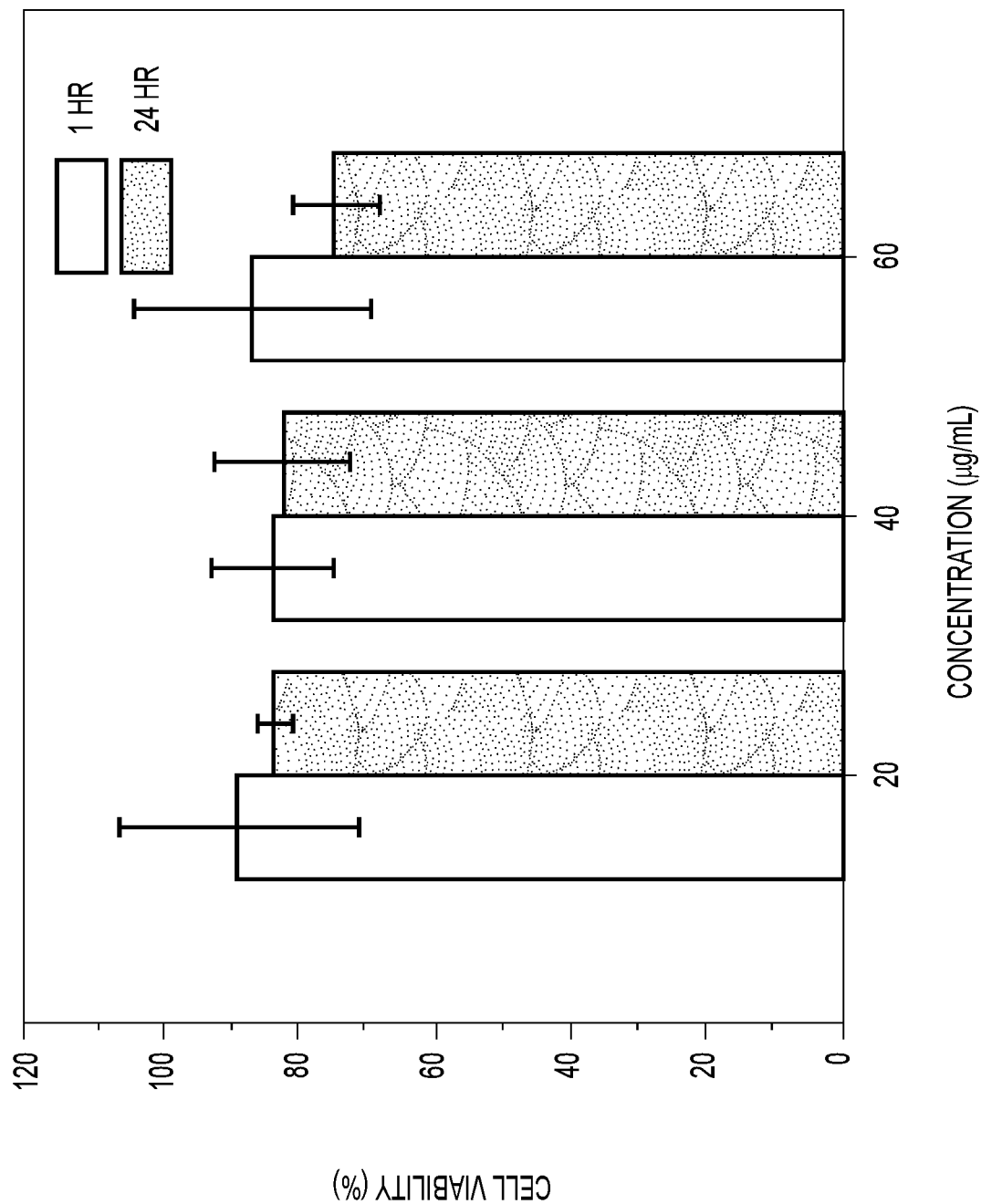

To test the cytotoxicity of PANs, MTT assay was performed on cultured neurons (DIV15-18) following incubation with PANs for 1 hour and 24 hours, respectively. FIG. 1J show cell viabilities over 80% were observed in all experimental groups with PAN concentrations ranging from 20 to 60 µg/mL, indicating low toxicity of PANs to neurons. To further test whether laser excitation introduces cellular damage and to determine the damage threshold for in vitro neural stimulation, a cell viability assay after laser application was also performed with Sytox Green nuclei staining (Jones and Singer, 2001). Neuron cultures at DIV 15-18 were incubated with 150 µL, 20 µg/mL PAN solution for 15 minutes. Nanosecond laser at 1030 nm was delivered to the culture via a 200 µm diameter optical fiber with 0.22 NA. Conditions of the pulsed laser include a pulse width of 3 ns, a repetition rate of 3.3 kHz, a laser train of 3 ms (corresponding to 10 laser pulses).

Figure 1K:
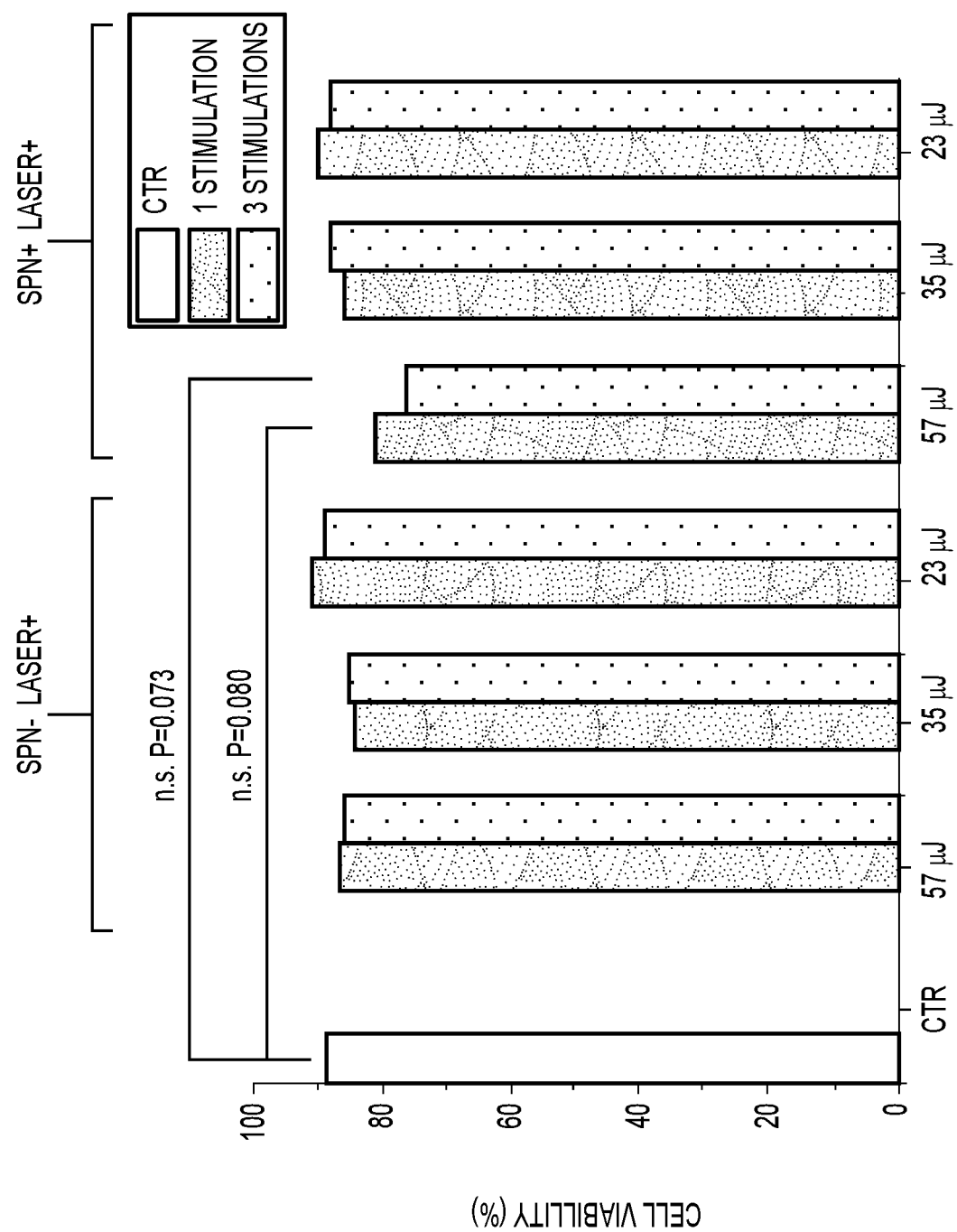

As shown in FIG. 1K, 1 hour after laser excitation, only neurons exposed to 57 µJ laser pulses showed slightly decreased viability, while neurons exposed to laser pulses of 35 and 23 µJ showed similar viability compared to neurons without PAN and laser exposure. Thus, a laser pulse energy of 17 µJ/pulse (pulse energy density of 2.1 mJ/cm$^2$) was selected for future stimulation experiments. The laser energy chosen is well below the damage threshold from the viability assay as well as ANSI (American National Standards Institute) standard for maximum permissible skin exposure (80 mJ/cm$^2$ per pulse). These results collectively show that negatively charged PANs can sufficiently bind onto neuronal membranes via a charge-charge interaction, without obvious cytotoxicity upon desired laser excitation.

Figure 2A:
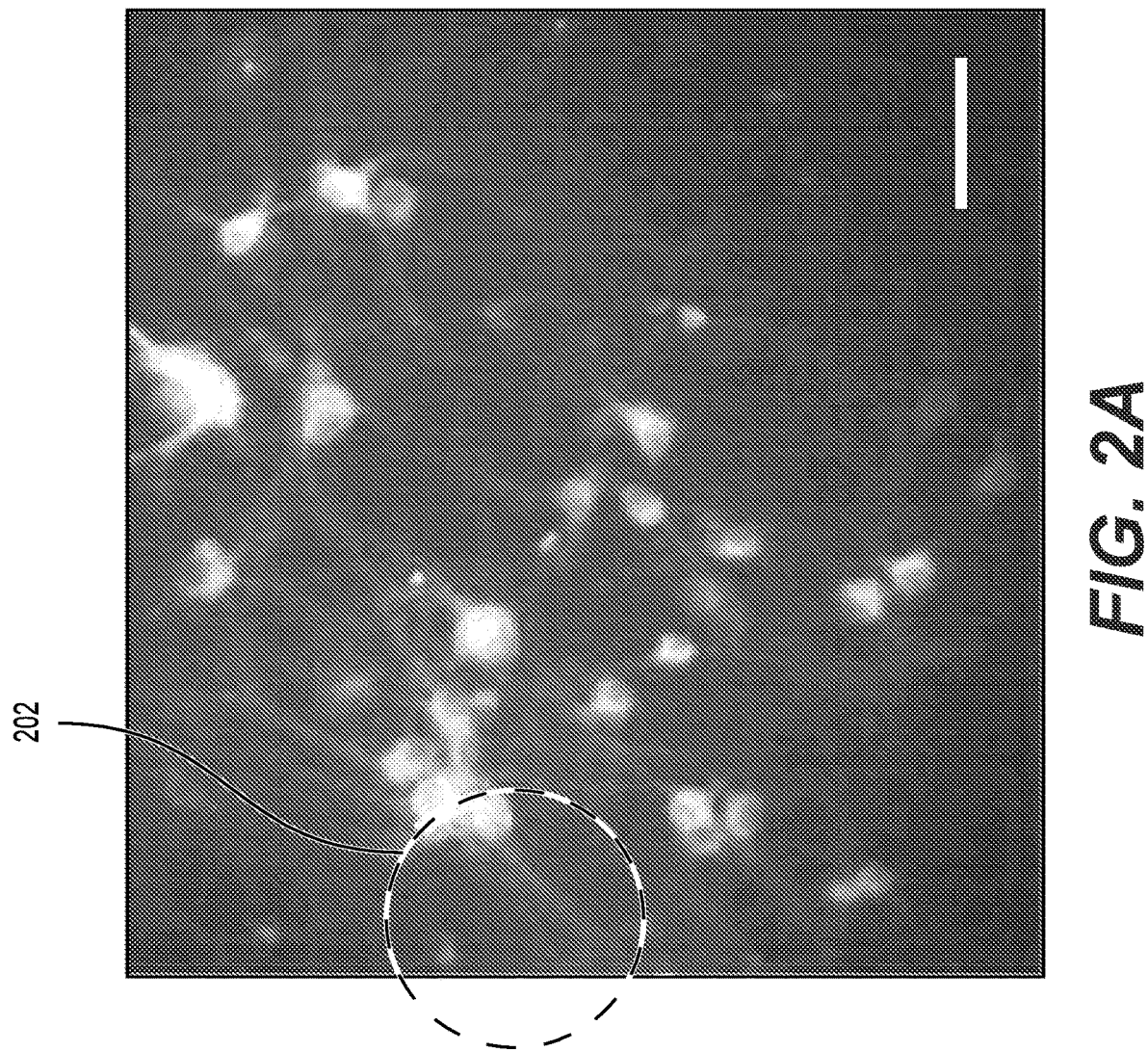

FIGS. 2A-2H illustrate PANs induced neural stimulation and corresponding results. After showing that PANs bind to neurons, their potential for neural stimulation was further analyzed. Calcium imaging was performed on Sprague Dawley (SD) rat primary cortical neurons transfected with GCaMP6f on a in house built wide-field fluorescence microscope. Imaging was performed on 5 culture batches for each group. Data from total 60 neurons, all of which were within 100 µm proximity to the surface of the fiber were analyzed. The 100 µm proximity was chosen based on the estimated illumination area of the optical fiber. A representative fluorescence image of the neuron culture is shown in FIG. 2A, with dashed circle 202 showing the position of the fiber. Increase in fluorescence intensity of GCaMP6f at individual neurons was clearly observed immediately after applying pulsed laser.

Figure 2B:
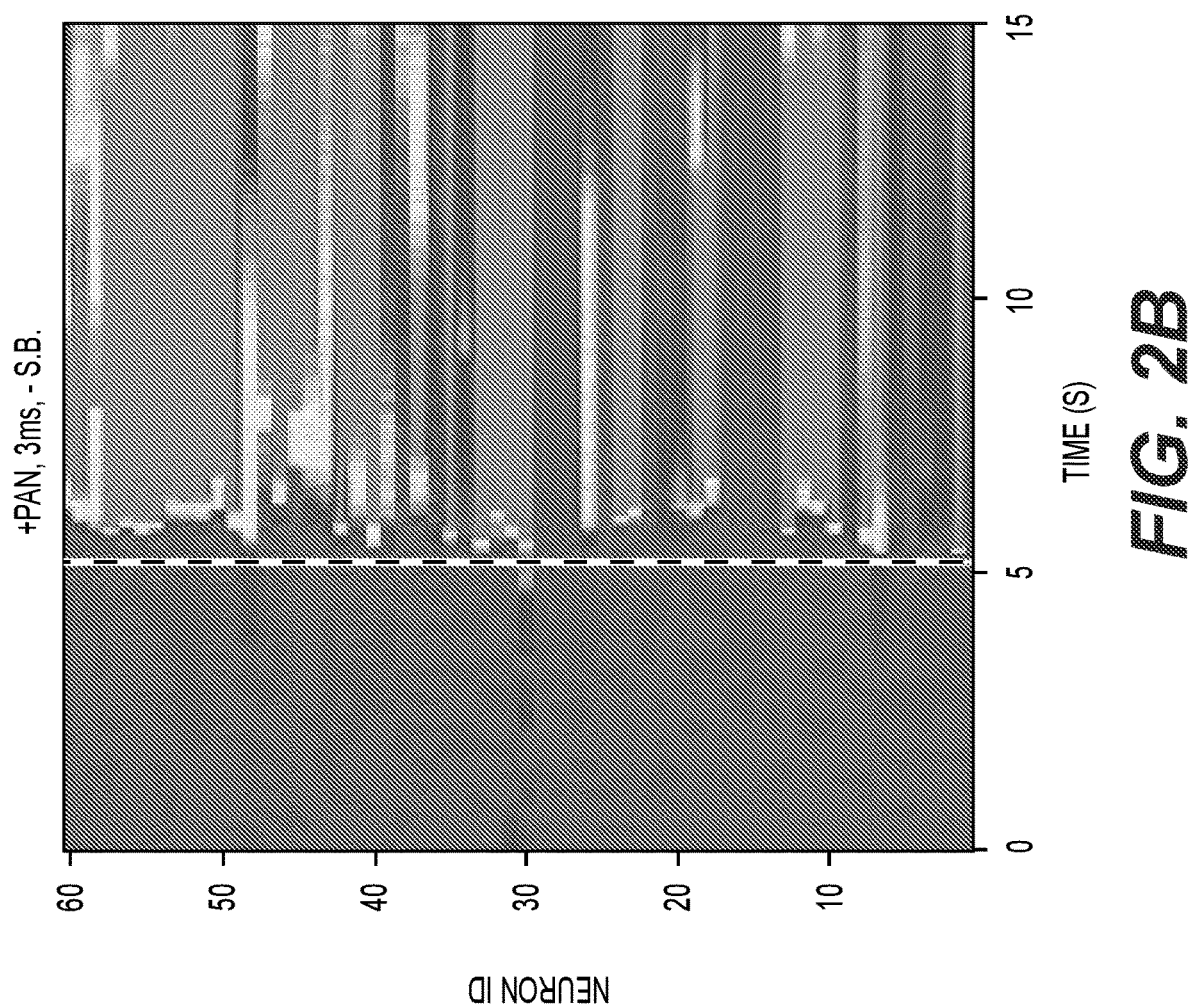

Out of total 60 neurons studied, 37 neurons showed an increase in fluorescence greater than 10% or F/F$_0$ ratio above 1.10 after the laser onset, as shown in FIG. 2B. F$_0$ is the baseline fluorescence signal of the neurons before the stimulation. Notably, two types of responses were detected, a transient response shown in FIG. 2C and a prolonged response taking longer time (up to 60 s) to recover to the baseline shown in FIG. 2D. The decay of the response curves was fitted exponentially and defined a time constant when they decrease by a factor of 1/e (e=0.368) from the peak fluorescence intensity. The transient activations typically show decay time constants ranging from 2 to 5 sec, while the prolonged activations have time constants of 5 sec and up. The success rate, defined as the percentage of activated neurons identified through the F/F$_0$ ratio above 1.10, was calculated. Under the 3 ms laser pulse train, total 62.5±21.3% of the neurons exhibited activations immediately after the nanosecond laser was onset. Specifically, 11.2±4.8% and 51.3±16.5% were observed as the transient responses and prolonged responses, respectively as shown in FIG. 2H.

To investigate whether the activations observed based on the increased fluorescence intensity are caused by action potential, a control experiment was performed with addition of 3 µM of Tetrodotoxin (TTX), a blocker of voltage-gated sodium channels. After addition of TTX, only a total of 6.7% neurons showed activation upon laser excitation, with 1.7±2.9% for transient activation and 5.0±5.0% for prolonged activation (FIG. 2E), indicating that the observed calcium transients were induced by firing of action potentials. As an additional control, only applying a nanosecond laser at the same laser condition without PANs induced activation with a success rate of 1.7±2.9%, indicating optical excitation through the nanosecond laser alone triggers negligible activities, as shown in FIG. 2F.

Figures 2G, 2H:
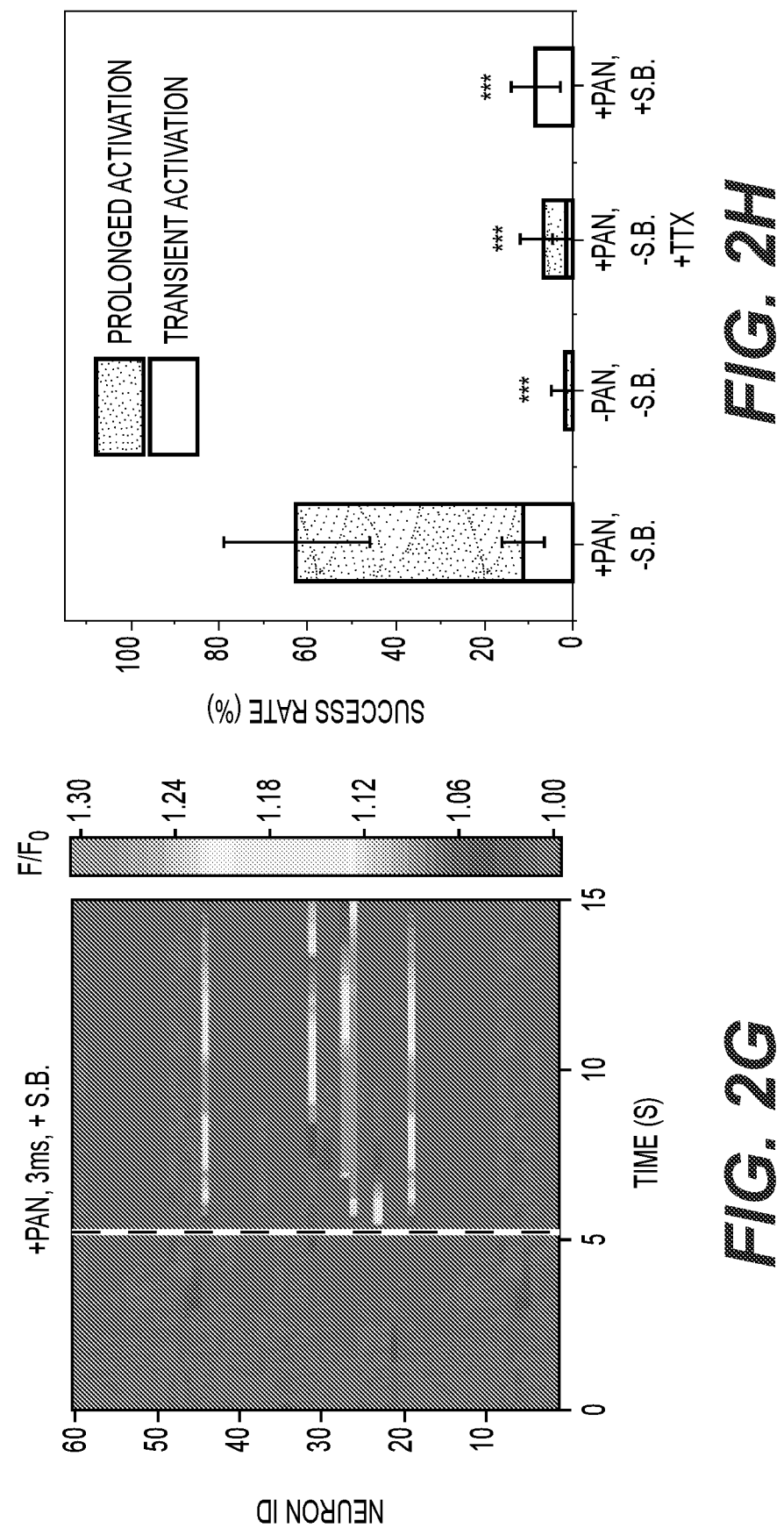

To investigate how synaptic inputs affects stimulation outcome, a cocktail of synaptic blockers (10 µM NBQX, 10 µM Gabazine and 50 µM DL-AP5) were applied and observed an overall success rate of 8.3±5.8%, a significant reduction from 62.5%, as shown in FIG. 2G. Interestingly, the remaining activation is dominantly transient activation, while prolonged activation is completely blocked by the cocktail. These results suggest that the transient activation is likely the result of direct PAN mediated stimulation, while the prolonged activation comes from a train of action potentials resulted from the activation of neural networks by synaptic transmission. Collectively, the results indicate that PAN-triggered neural activities are action potential-dependent and involve synaptic transmission.

FIGS. 3A-3D illustrate the spatial distribution of neuron activation induced by PAN. FIG. 3A shows the fluorescence images of neurons before stimulation using GCaMP6f. FIG. 3B shows the maximum ΔF/F$_0$ image of the field of view after PAN stimulation. FIG. 3C shows the single neuron targeting with a tapered fiber. FIG. 3D shows the maximum ΔF/F$_0$ image of the field of view after PAN stimulation. The dash lines indicate the position of the optical fiber 302 and the tapered fiber 304.

Notably, no activations were found outside the illumination area of the optical fiber, as shown in FIGS. 3A and 3B. Aiming to achieve neural stimulation at single neuron precision, a tapered optical fiber 304 was applied with a tip diameter of ~10 µm, placed close to the neuron of interest, as shown in FIGS. 3C and 3D. Upon light illumination, only the targeted neuron showed strong calcium activation, while other neurons in the field of view remain unchanged. These results indicate that the spatial resolution of PAN stimulation is defined by the illumination of the pulsed light, which makes it possible to achieve neural stimulation at optical resolution through focusing of excitation light.

Key parameters to control the stimulation through PANs include laser conditions and binding density of PANs on neurons. To understand the effect of the pulsed laser train on activations by PANs, the activation was first analyzed under increased laser pulse train of 5 and 10 ms, corresponding to 17 and 33 laser pulses, respectively. In the laser only groups, the overall success rate was found to be 3.3±2.0% using 5 ms, and 18.3±10.4% for 10 ms (N=60, 3 different culture batches), dominated by the prolonged activation. With PANs cultured for 15 min with neurons, under the 5 ms laser duration, an overall success rate of 66.7±14.4% was observed (N=60, 3 different culture batches). When the laser pulse train increased to 10 ms, the total success rate was found to be 80.0±15.3%. Notably, both 5 ms and 10 ms laser pulse trains produced neural activities dominated by prolonged activation. The 3 ms pulse train sufficiently produced a high successful rate in direct activation with a less network effect. Therefore, one may identify it as the optimal laser pulse train for PAN mediated neural stimulation for following experiments.

To investigate how the binding density impacts PAN mediated stimulation, the incubation time of PANs with neuron cultures was varied. In the group where the stimulation was performed immediately after addition of PANs followed with rinses, no neural activation was detected. This observation confirmed that only bound PANs can trigger the activation. In the group where the stimulation was performed after PANs were incubated with neurons for 1 hour, 20.0±18.0% neurons exhibited transient activations and 28.33±16.07% exhibited prolonged activation. These results indicated 15-minute culture time provides a binding density sufficient to trigger neural stimulation.

To enable specific targeting for stimulation, the PANs is bioconjugated with antibodies to specifically target the mechanosensitive ion channel transient receptor potential cation channel subfamily V member 4 (TRPV4). TRPV4 was chosen based on its high expression rate on the neuronal cell membranes and its capability in sensing external mechanical stimuli.

Figure 4A:
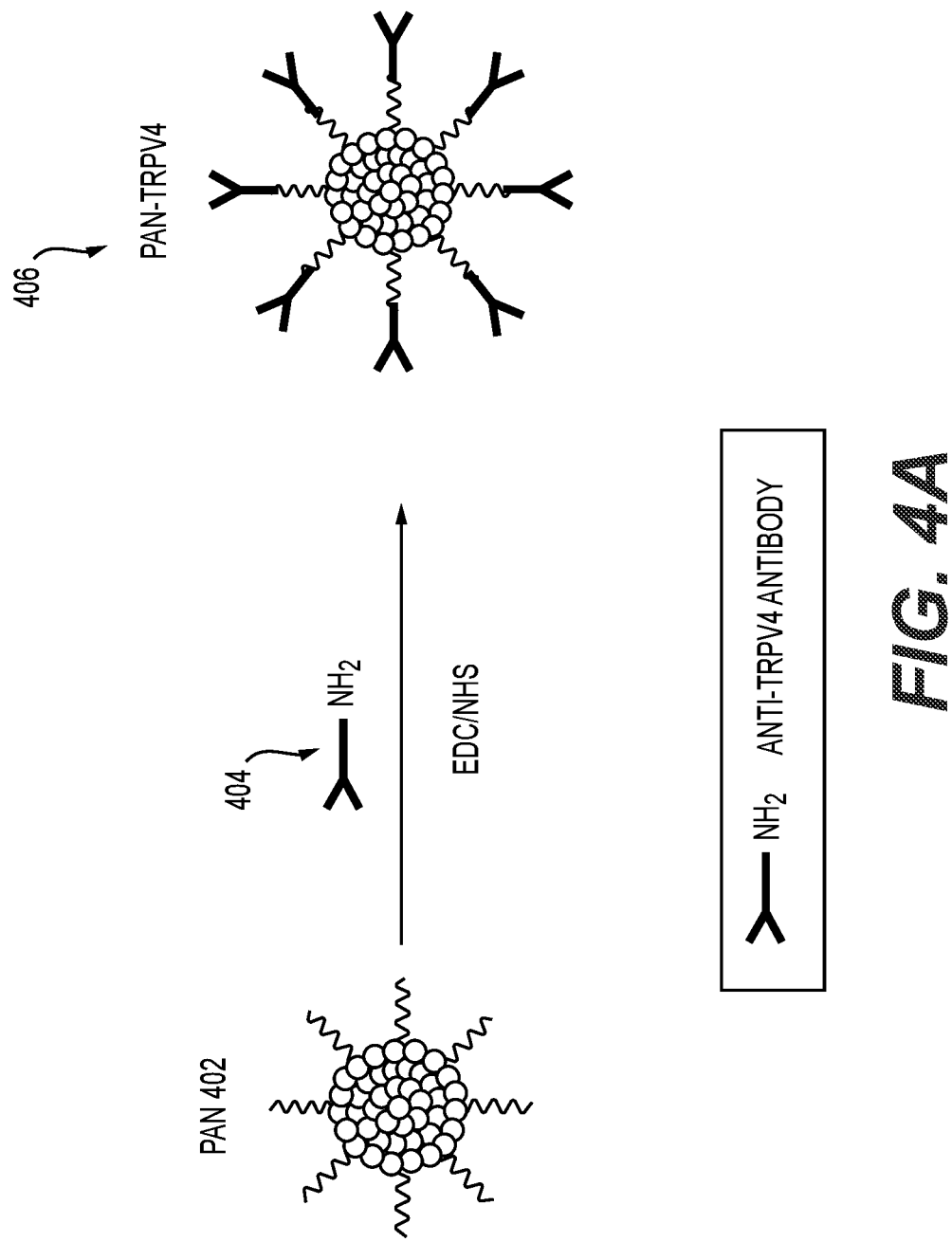
FIGS. 4A-4H illustrate the PANs-TRPV4 406 induced transient activation of neurons and corresponding results.
Figure 4B:
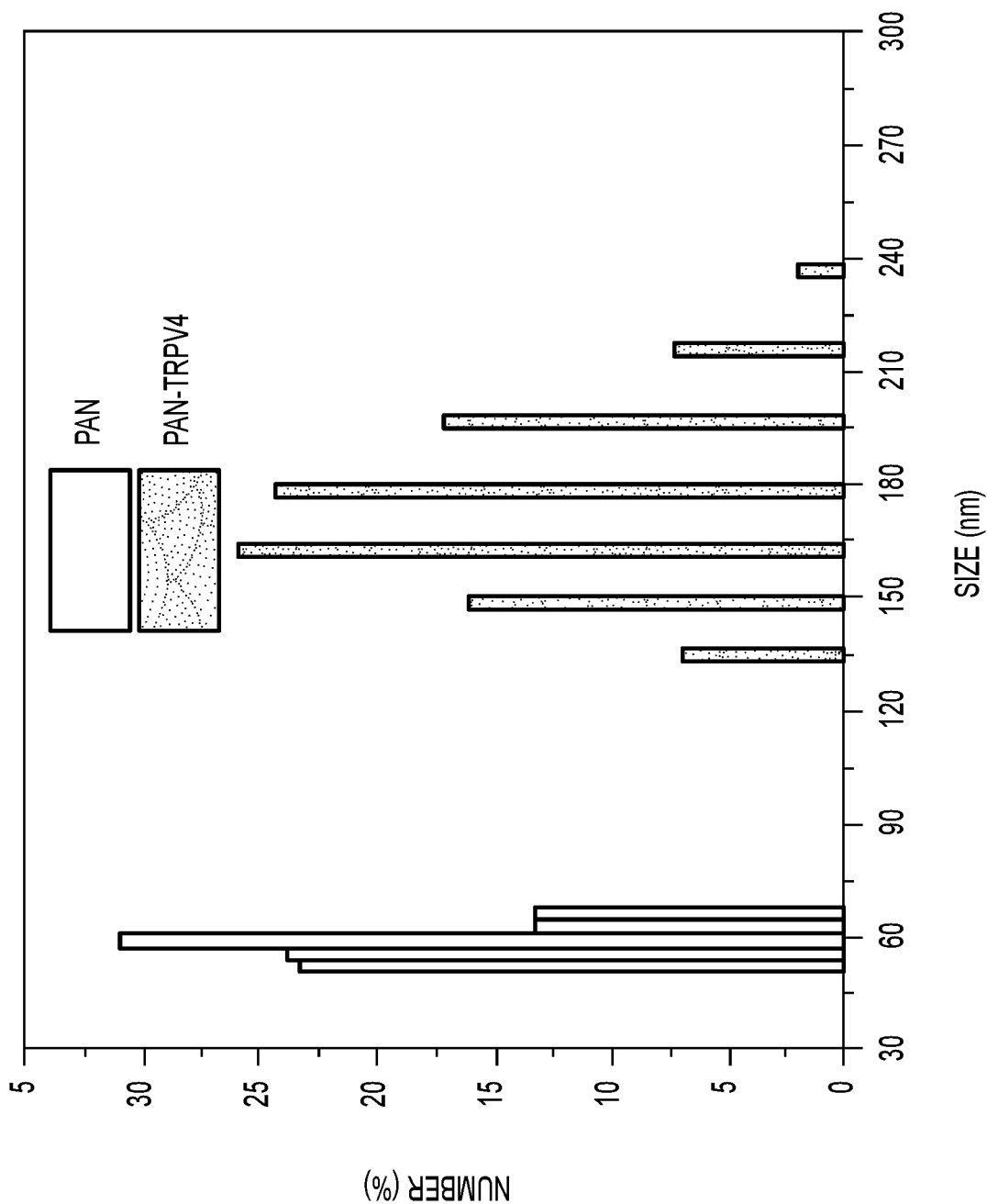
Figure 4C:
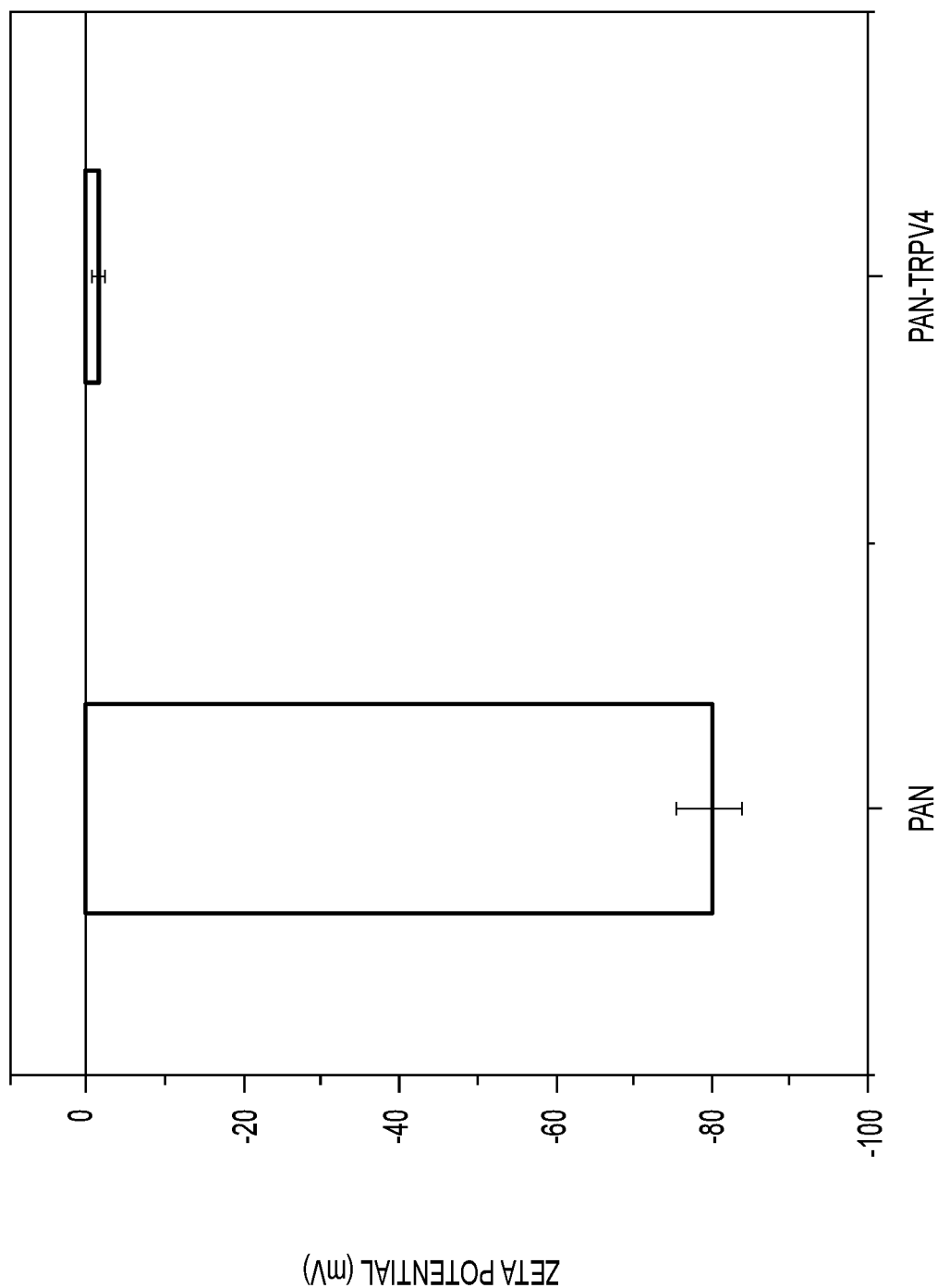

FIGS. 4A-4H illustrate the PANs-TRPV4 406 induced transient activation of neurons and corresponding results. In this case, PANs 402 may be conjugated with anti-TRPV4 antibody 404 through a carbodiimide coupling reaction, using ethyl(dimethylaminopropyl) carbodiimide (EDC) and N-hydroxysuccinimide (NHS), between the carboxyl group on PANs to the amine group on the antibody 404, as shown in FIG. 4A. Successful bioconjugation was confirmed by comparing characteristics of PANs and anti-TRPV4 conjugated PANs (PANs-TRPV4) 406. A size increase from 59.4±5.3 nm to 181.8±36.7 nm was revealed by DLS analysis, as shown in FIG. 4B. The zeta potential for PAN-TRPV4 is −1.49±0.38 mV, almost neural, distinct from PAN (FIG. 4C). No change was noticed in the PAN-TRPV4 solution. No obvious shift in absorption spectrum was identified for the PAN-TRPV4 solution.

Figure 4D:
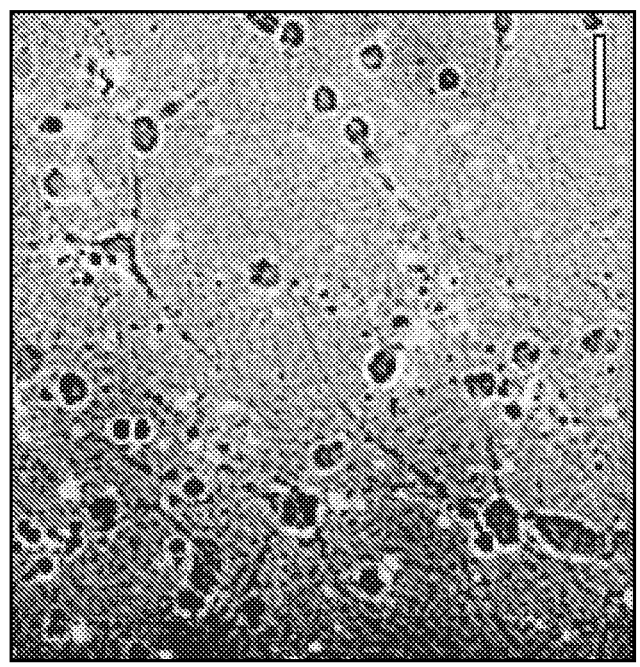

The expression of the TRPV4 channels was confirmed in the membrane of embryonic cortical neurons. A large number of target sites on the neuronal membrane may be available for PANs-TRPV4 for potential binding. After incubation with PANs-TRPV4 for 15 minutes under the same condition as for PANs, PANs-TRPV4 binding to neurons were visualized by TA microscopy, as shown in FIG. 4D. The PAN-TRPV4 density was estimated to be 43.8±20.8 per soma, slightly larger than that found for PAN binding.

Figure 4F:
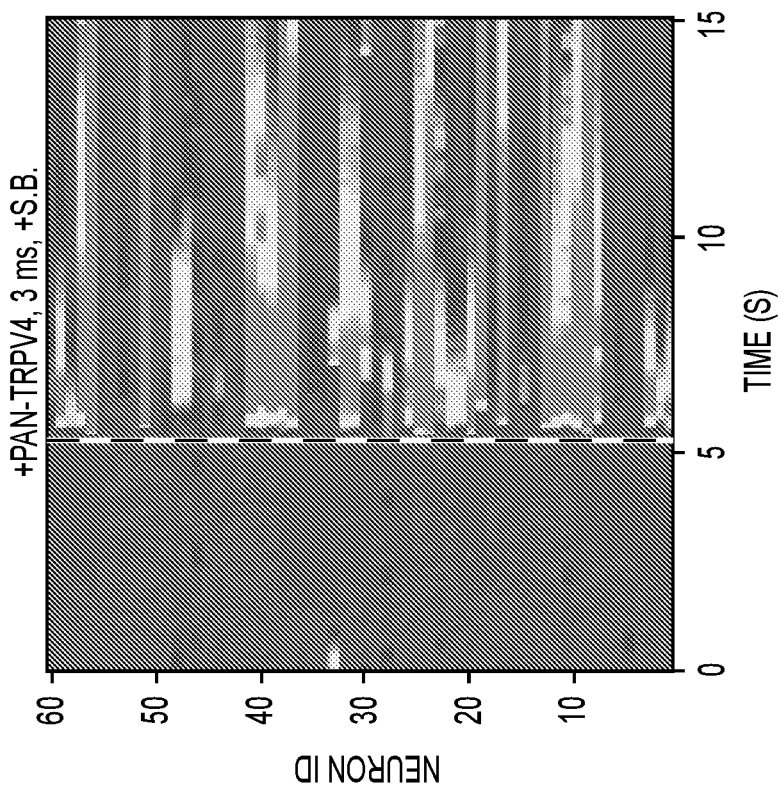
Figure 4E:
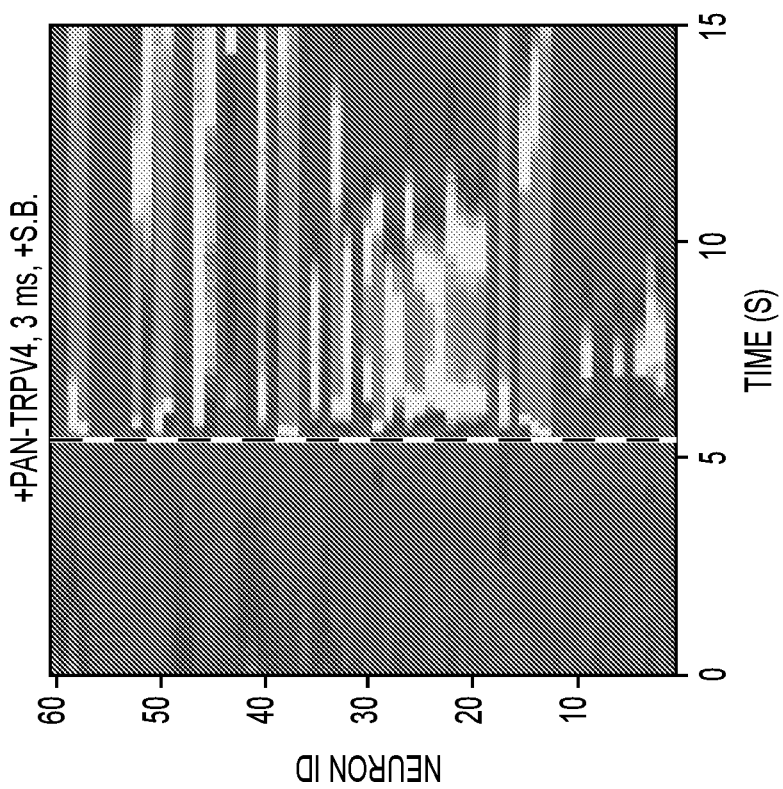

Next, it is determined whether the PAN-TRPV4 could improve the specificity of neural stimulation through direct activation of the TRPV4. Under the same experimental condition used for PANs, 60 neurons collected were analyzed from 5 different culture batches. As shown in FIG. 4E, neural activations induced by PAN-TRPV4 show an overall success rate of 55.0%, of which the transient stimulation responses is 50.0±5.0% and the prolonged response is 5.0±5.0%. Although the overall success rate of PAN-TRPV4 is reduced slightly compared to PAN, the portion of transient activation increased substantially. As shown in FIG. 4F, with the application of synaptic blocker cocktail, the overall success rate remains as 53.3%. 51.7±12.6% of neurons showed transient activation and only 1.7±2.9% showed prolonged activation, which indicates that PAN-TRPV4 induces more direct activation through targeting TRPV4 without significant involvement of neural network and synaptic transmissions. To validate that the observed activation is mediated by the activation of the TRPV4 channel, the TRPV4 channel blocker, GSK 2193874, was added into the culture, prior to adding PAN-TRPV4 solution (N=30, collected from 3 different culture batches).

Figures 4G, 4H:
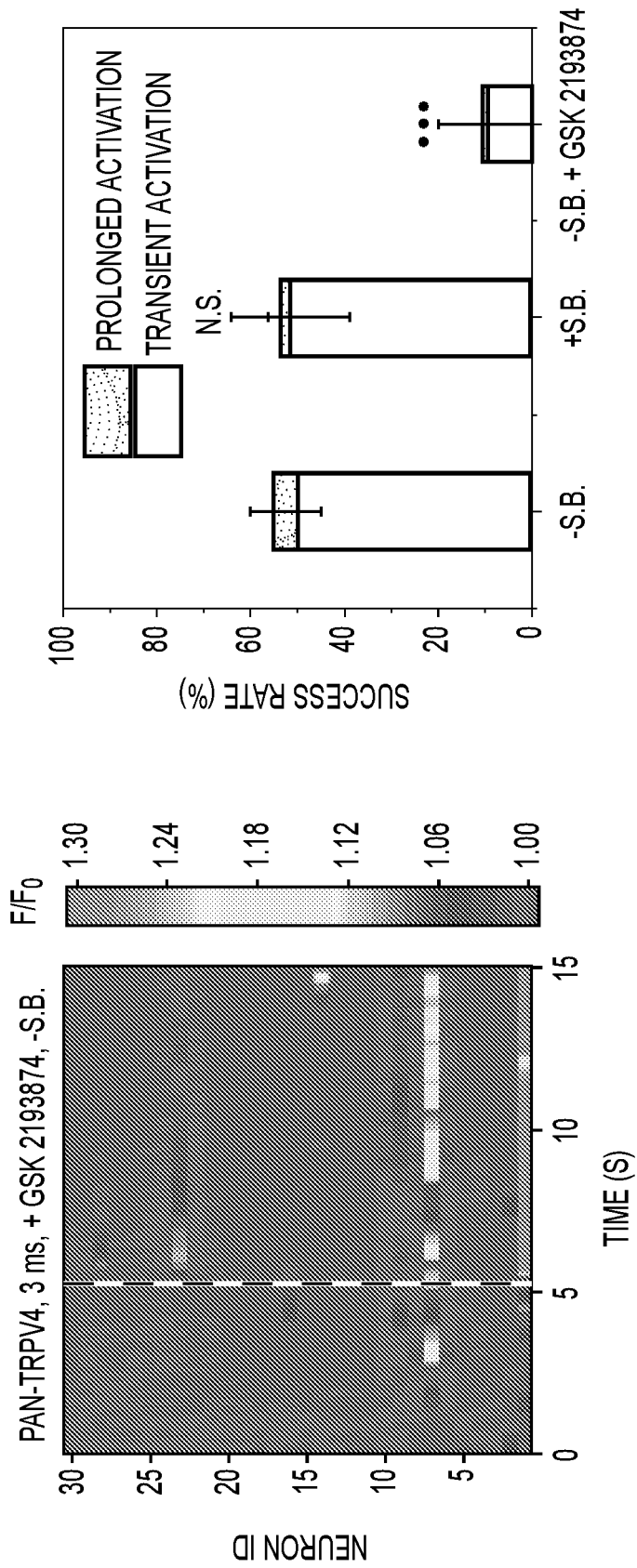

As shown in FIG. 4G, with the presence of GSK 2193874, the success rate significantly decreased, with 10.0±10.0% of the neurons showing transient response and no prolonged activation was detected, as shown in FIG. 4H. Neurons were further stimulated with repeated photoacoustic stimulation use PAN-TRPV4. 4 bursts of laser pulses, with a 3 ms duration in each burst and 10 s inter-burst interval, were delivered to the neurons cultured with PAN-TRPV4 for 15 minutes. Consistent calcium activations were observed. These results collectively show that PAN-TRPV4s enabled a specific stimulation directly through the TRPV4 ion channel.

Upon successful stimulation of cultured primary neurons, it is determined whether PANs could activate neurons in vivo in living animals.

Figure 5A:
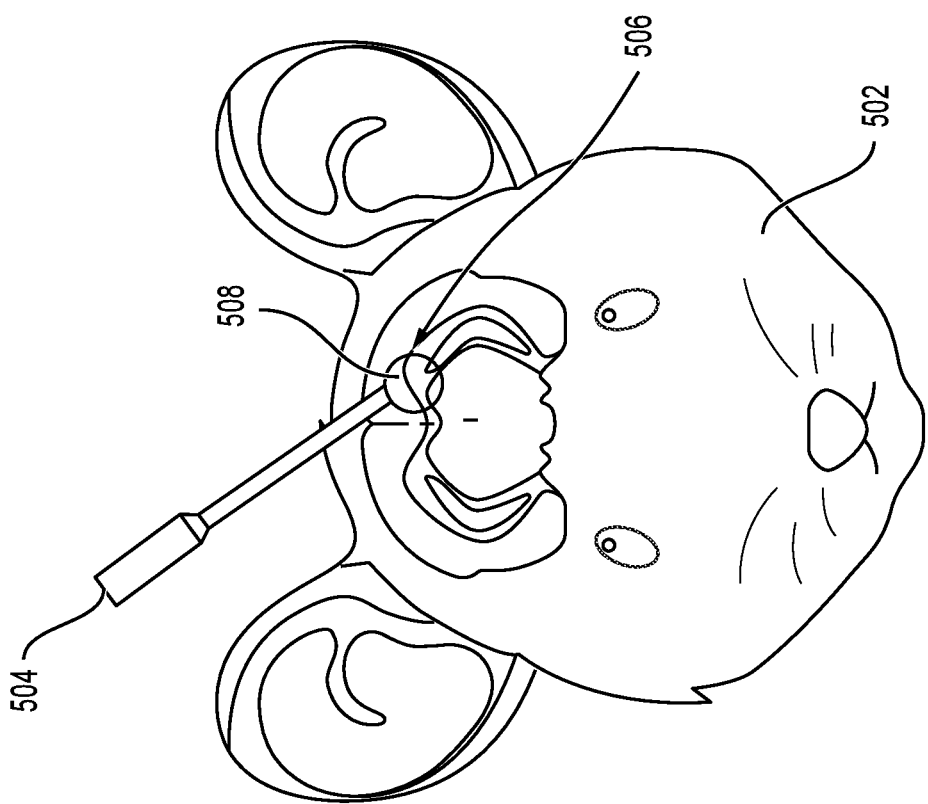

FIGS. 5A-5D illustrate in vivo neural stimulation by injected PANs and corresponding results. In particular, FIG. 5A shows a 600 nL of 1.0 mg/mL PAN solution may be injected into the primary motor cortex of C57BL/6 mice 502 using a stereotaxic injector at a controlled speed of 20 nL/min. Stimulation was performed 1 hour after the injection user laser 504 illuminating with a wavelength of 1030 nm. To validate brain activation, local field potential (LFP) recording was performed at the PAN injection site 506 using recording electrode 508. To avoid electric artifact produced by laser radiation, recording electrode 508 may include multifunctional fibers with a thick polymer coating. As shown in FIG. 5B, a 3 ms laser pulse train at 21 mJ/cm$^2$ produced strong LFP response on the stimulated cortex 510, while in the control group 512 on the contralateral side without PAN injection, the laser irradiation did not produce any response.

Figure 5C:
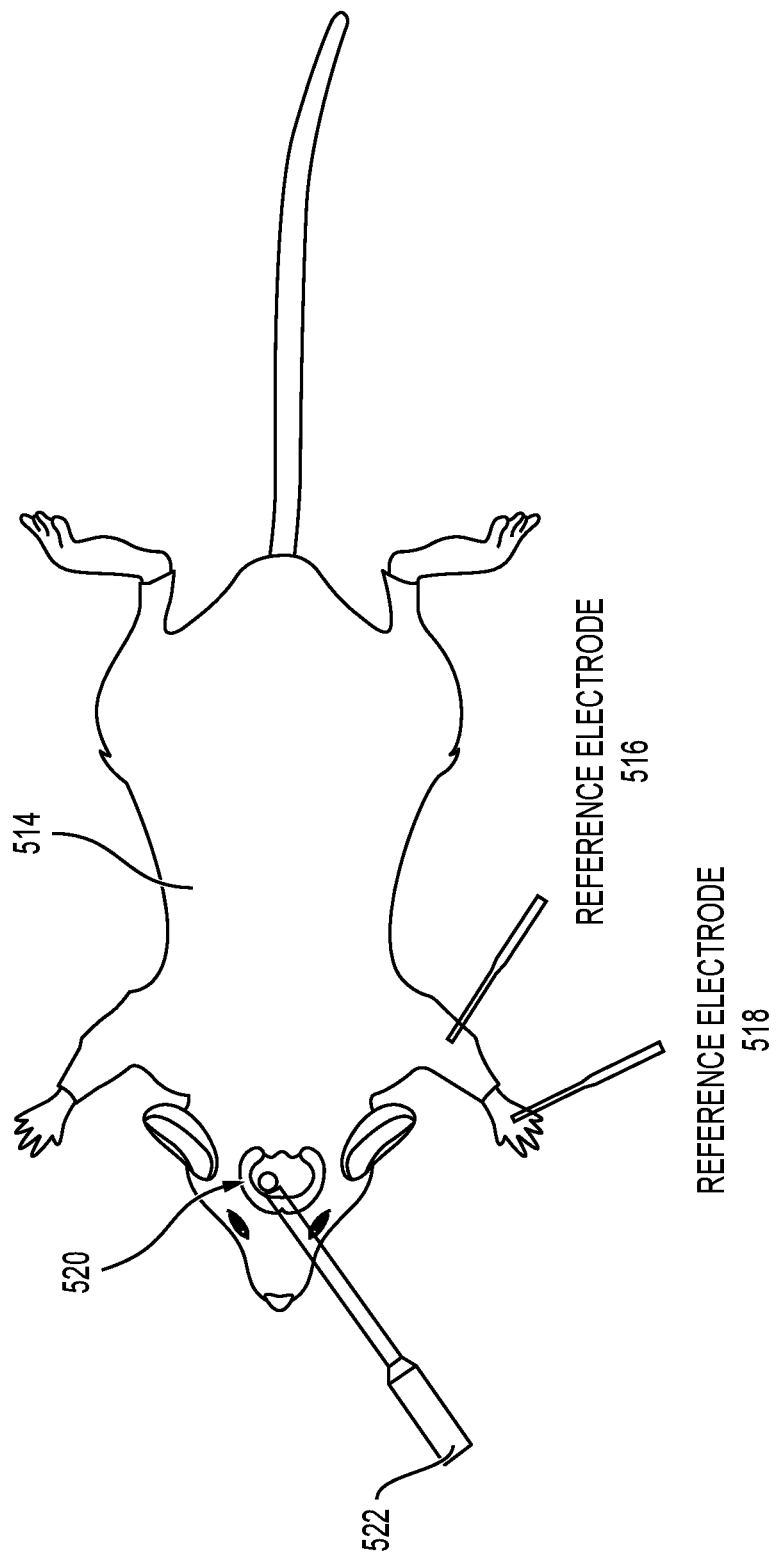
Figure 5D:
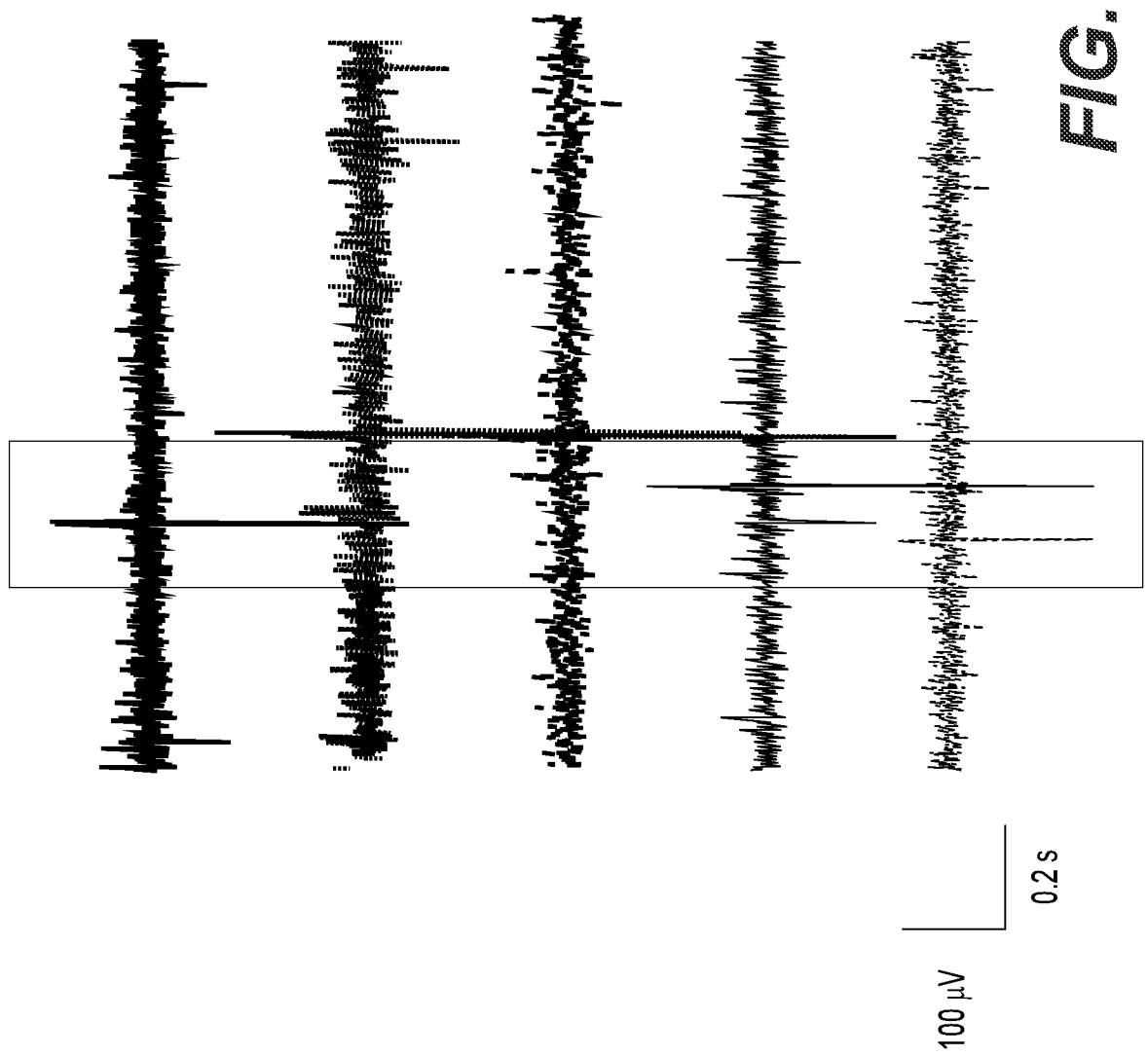

With successful LFP recording of PAN stimulation in the brain, the behavior outcome of the stimulation was further evaluated. FIG. 5C shows an electromyography (EMG) being performed as a measurement of the effect of PAN brain stimulation. A 600 nL PAN solution at 1.0 mg/mL was injected to the primary motor cortex of the mouse 514. At 1 hour after the injection, a recording electrode 516 was inserted subcutaneously and parallel to the forelimb triceps brachii muscle. A reference electrode 518 was inserted in the footpad with a ground electrode inserted subcutaneously on the trunk and ipsilateral to the stimulation site. A 200 ms laser pulse train was delivered, via laser 520, to the injection site 522 through an optical fiber. EMG responses with an amplitude of 428.8±119.0 µV, with a delay of 127.8±24.3 ms, were recorded and shown in FIG. 5D. These results suggest that the PAN mediated brain stimulation was sufficient to induce motor cortex activation and invoke subsequent motor responses.

The photoacoustic effect is known to associated with a temperature increase. To gain insights on how much the photothermal process might contribute to the successful activation discussed above, neuron stimulation was performed under continuous wave (CW) laser. The CW laser excitation of nanoparticles is known to produce a photothermal effect resulting a local temperature rise without generation of photoacoustic signals. By comparing neural response to PANs upon excitation by the CW laser to that by the nanosecond laser at the same power, one can determine whether PAN mediated stimulation differs from nanoparticle mediated photothermal stimulation. Since PANs absorb broadly in the range of 800 to 1800 nm, a CW laser at 1064 nm may be used. Identical neuronal culture conditions were used.

Figure 6A:
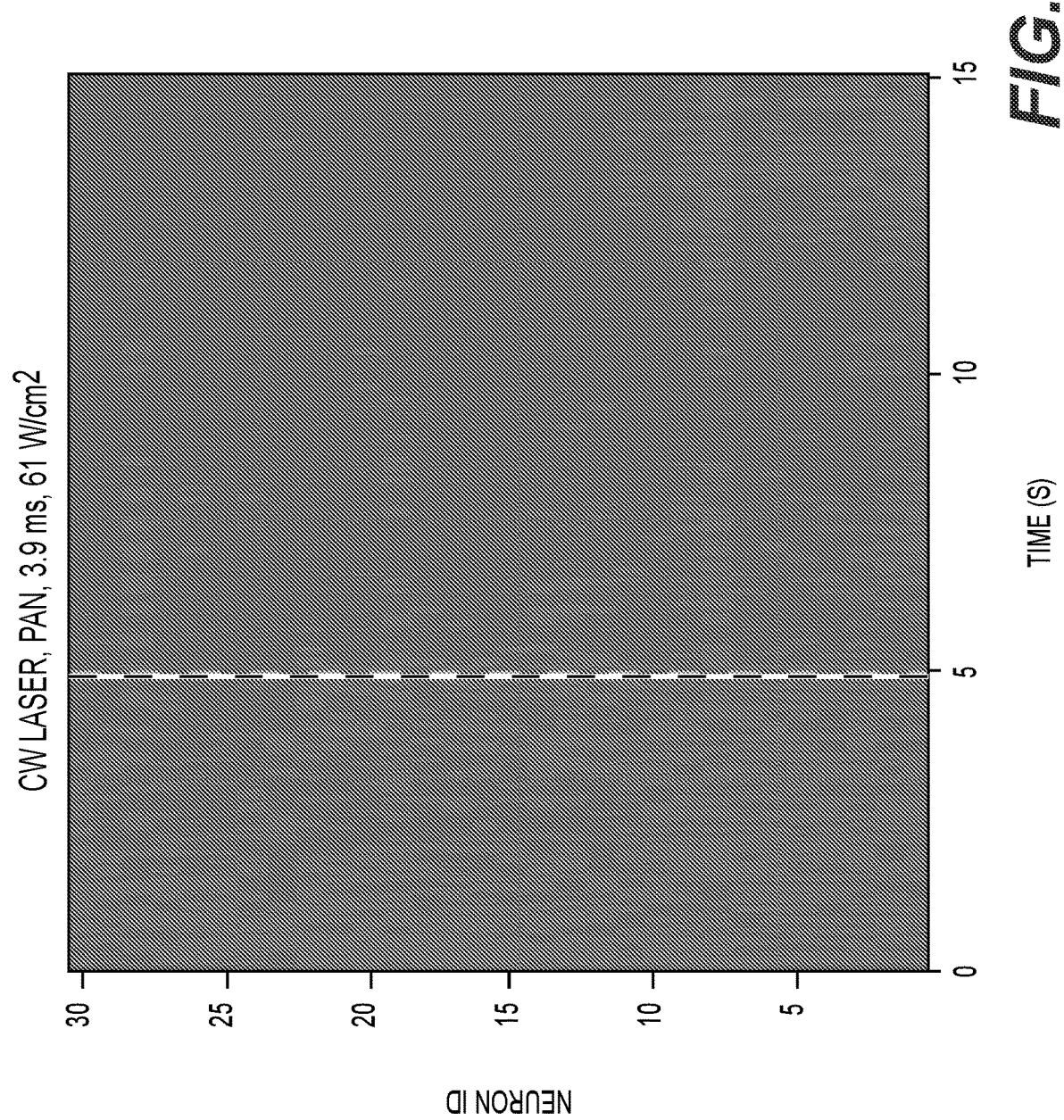

FIGS. 6A-6F illustrate PAN-mediated neural stimulation not thermally induced. While successful neural activation was achieved under a nanosecond laser power of 70 W/cm$^2$ and a train of 10 pulses over 3 ms, FIG. 6A shows no activation was detected using CW laser excitation with the laser power of 70 W/cm$^2$ over 3.9 ms duration (N=30, 3 different cell culture batches). Moreover, FIG. 6B shows no activation was observed as the CW laser power was increased to 397 W/cm$^2$ while maintaining the CW laser duration at 3.9 ms (N=30, 3 different cell culture batches). Activation of neurons was only observed when the duration was increased to 2.5 s and laser power was increased to 397 W/cm$^2$ (N=20, 3 different cell culture batches). These results show that under the CW laser at comparable power and duration to nanosecond laser conditions, the photothermal effect produced by the PANs alone cannot result in neural activation. The photoacoustic function of PANs enabled by the nanosecond light pulse contributed dominantly to the activation.

Figure 6C:
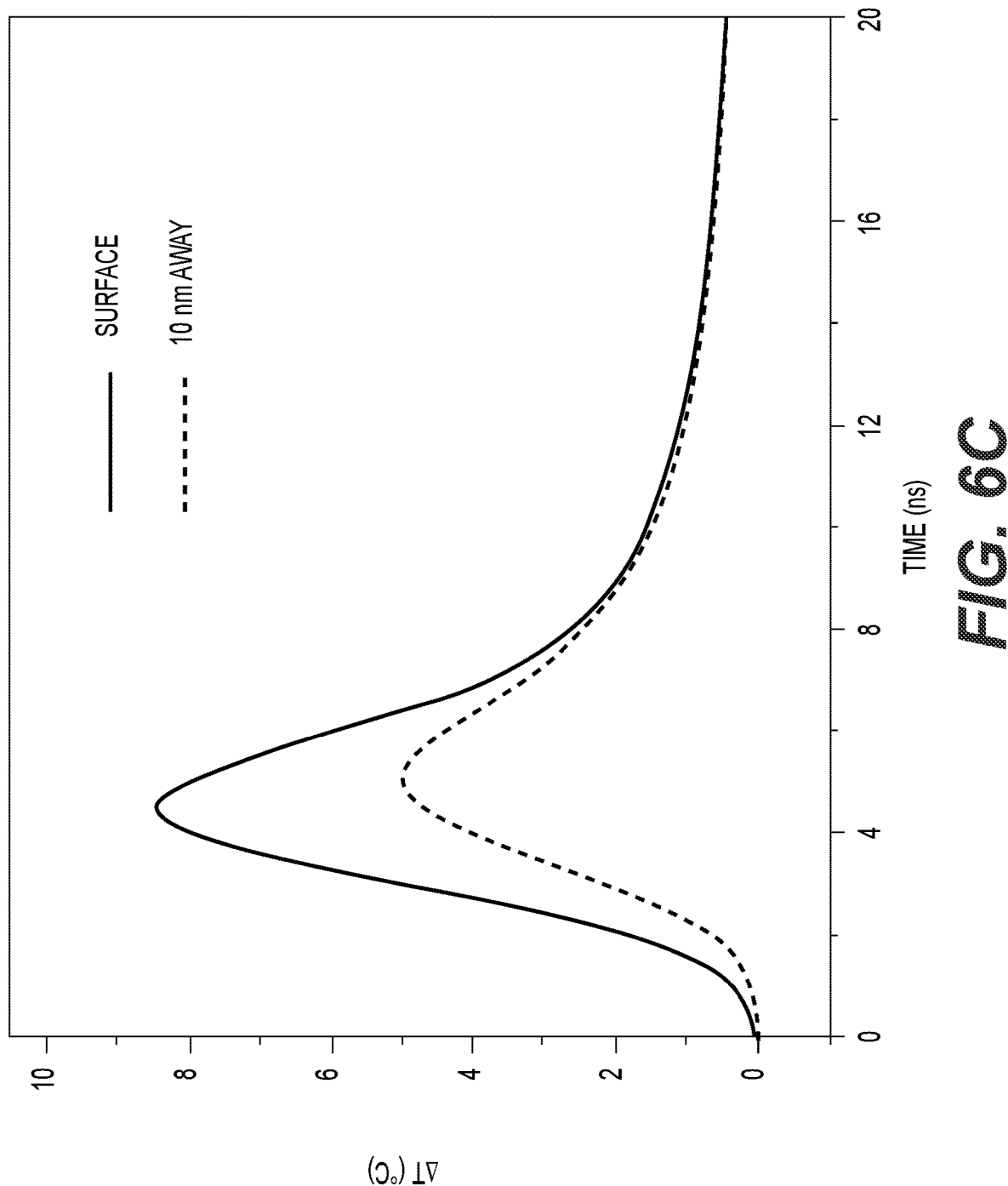
Figure 6D:
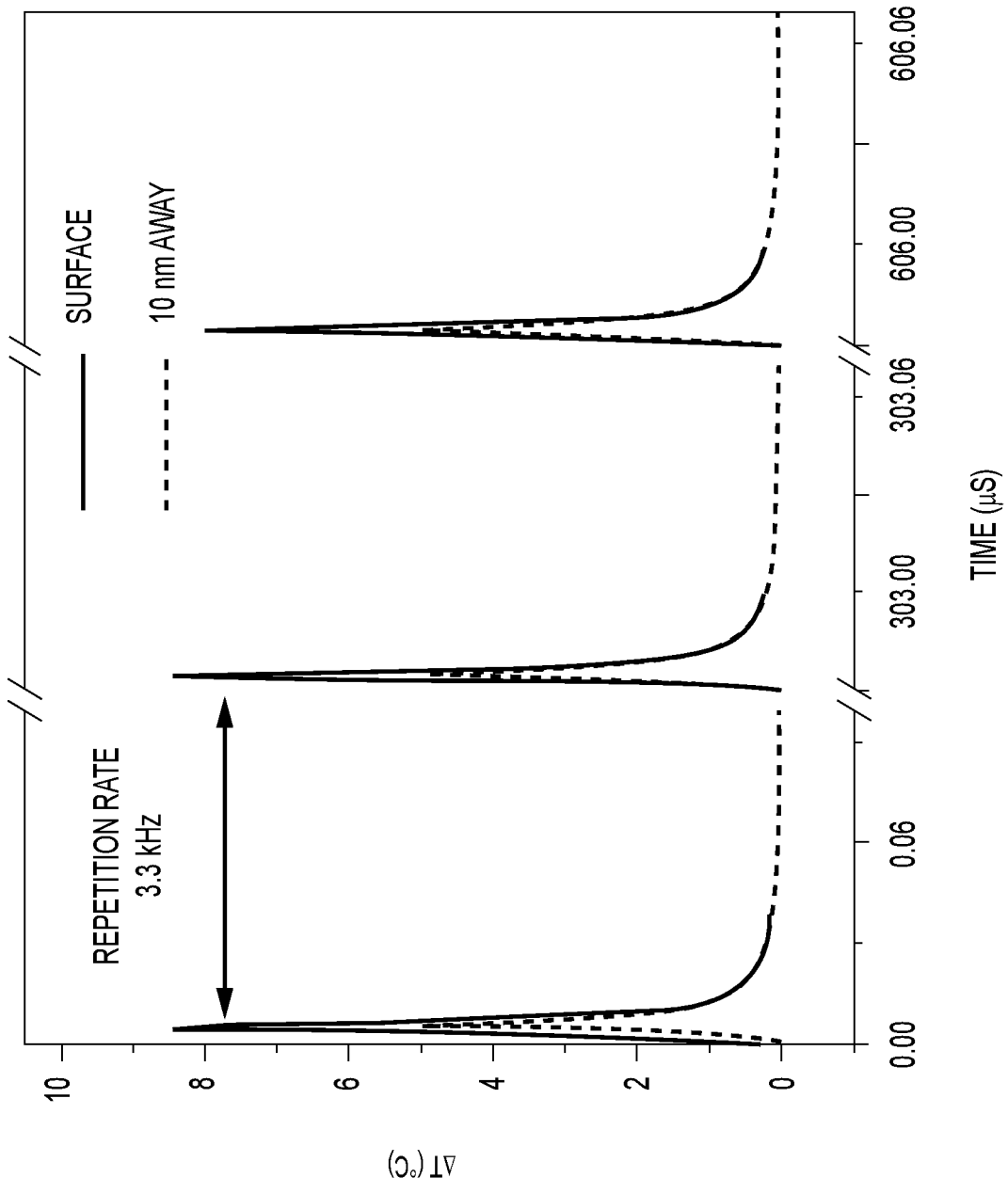

To understand how temperature rises and dissipates upon ns laser excitation of a nanoparticle, finite element modeling was applied to simulate the evolution of PAN surface temperature in water. Simulation for temperature at 10 nm away from surface of PAN in water was also performed, aiming to probe the temperature of neuron membrane where a PAN binds to. FIG. 6C shows how the PAN temperature evolves under excitation by a single 3-ns laser pulse at 1030 nm. Pulse energy density of 2.1 mJ/cm$^2$ was used, consistent with the condition used in the PAN stimulation experiments. Temperature increase is found to quickly rise to a peak value of 8.4° C. on the PAN surface (graph 602) and to 5.0° C. at 10 nm away from the PAN surface (graph 604), respectively. Importantly, in both cases, temperature decays to the baseline within 10 nanoseconds from the peak value. The laser pulse train used for PAN stimulation is operated with a repetition rate of 3.3 kHz. At this repetition rate, the laser pulse train resulted in pulsed temperature spikes with a FWHM of 3 nanoseconds and no temperature accumulation was observed, as shown in FIG. 6D.

Figure 6E:
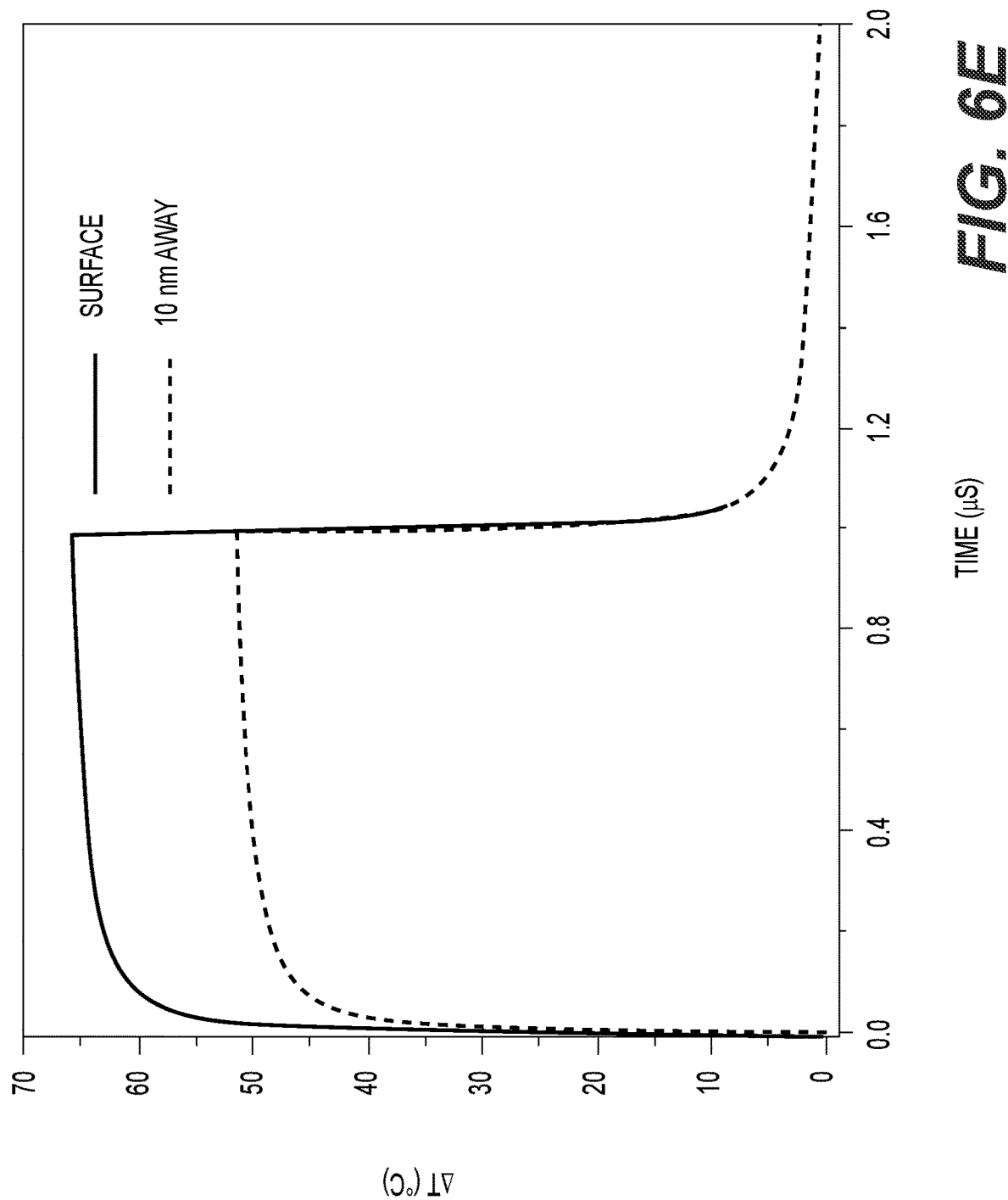
Figure 6F:
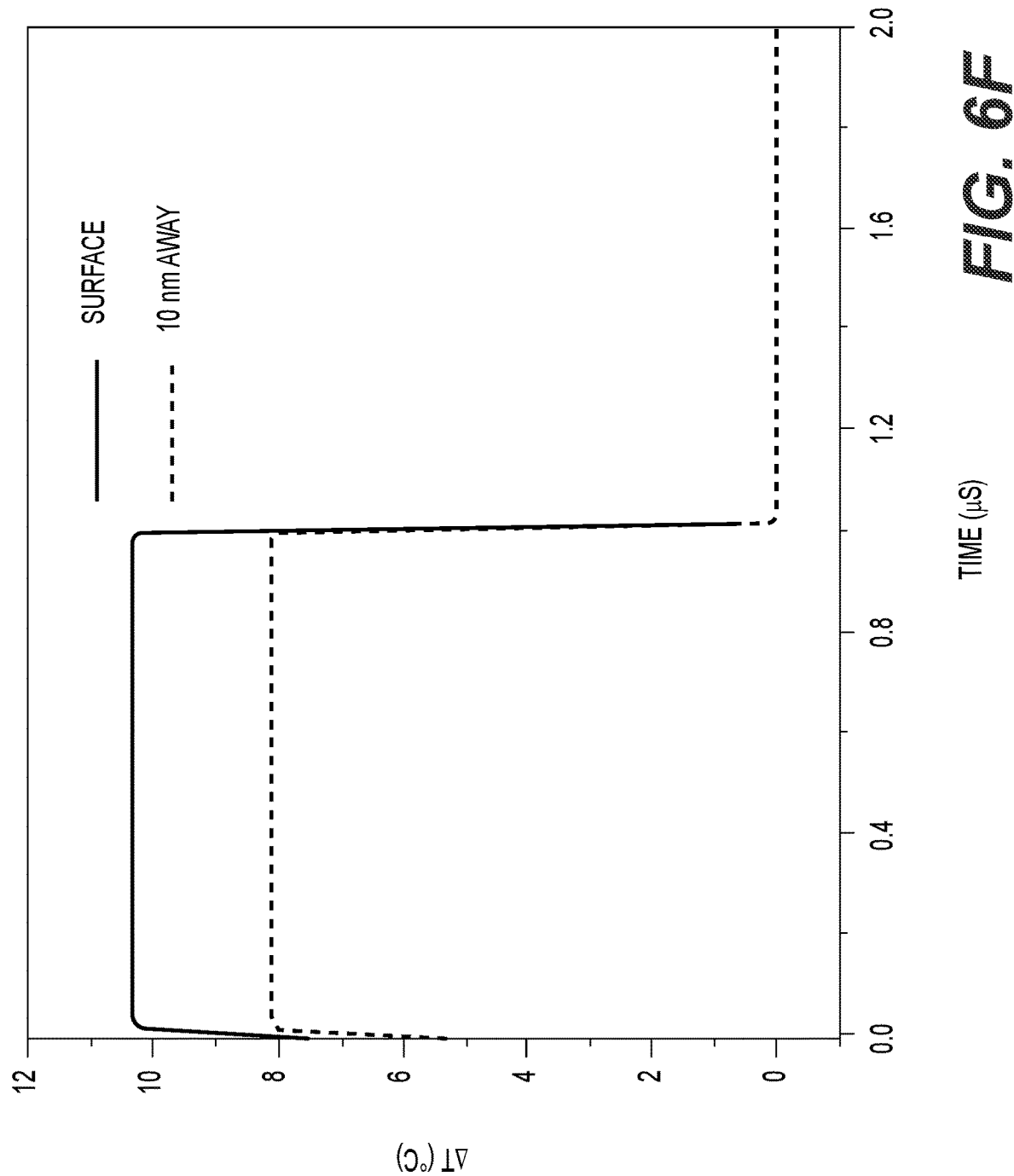

For comparison, the temperature evolution was simulated for gold nanoparticles of 60 nm diameter under a 532 nm CW laser with conditions reported for successful photothermal driven optocapacitive stimulation. Two conditions, one with energy of 67.8 nJ and duration of 1 µs and the other with energy of 9.8 µJ and duration of 1 ms, respectively, were used with a laser focus of 5 µm diameter as previously described. FIGS. 6E and 6F show the temperature profile under these laser excitation conditions was found to be substantially different from the temperature profile under the nanosecond laser excitation. As shown in FIGS. 6E and 6F, the temperature increases on the Au nanoparticle surface quickly reach a plateau within the first 200 ns in both CW laser cases, with plateaued values at 65.6° C. and 10.3° C., respectively. Similar temperature features also found in the simulation of graphite microparticles under a laser energy of 0.7 µJ for 80 µs laser duration at 532 nm, consistent with reported experimental and calculation results.

In summary, in the PAN case, the maximum temperature increase is significantly smaller than both CW cases. Additionally, the duration of each temperature spikes is a few nanoseconds, more than 2 orders smaller than that found for nanoparticle under CW laser excitation. It is conceivable that current induced by capacitance change over these tens of nanoseconds can be negligible. Together, the results suggest that the PAN stimulation is distinct from the photothermal optocapacitive stimulation.

A semiconducting polymer-based PANs for neural stimulation under excitation by a nanosecond laser at NIR-II window is provided. Enhanced specificity was achieved via bioconjugating TRPV4 to the PANs. Successful in vivo activation through PANs directly injected into the cortex area of mouse living brains was demonstrated by LFP and EMG recording.

The photothermal effect of nanoparticles has been reported to successfully modulate neurons mainly in vitro. Two potential stimulation mechanisms were proposed, one through the increase of temperature, with highest temperature often found in the range of 50° C. to 70° C., and another through an optocapacitive stimulation determined by the rate of temperature change. Excited by a 3-nanosecond pulsed laser, the maximum temperature rise on the PAN surface is 8° C. and temperature change is in the form of 10 spikes, each of which is less than 10 nanoseconds in duration, without temperature accumulation over 3 ms. Instead, the PANs are able to generate a localized acoustic wave on the microsecond scale upon a nanosecond pulsed light with a peak-to-peak pressure of 58.2 Pa at 10 nm from the PAN surface. Activation may not occur when the nanosecond laser was changed to a CW laser of the same energy. In addition to its mechanosensitivity, TRPV4 is also sensitive to mild temperature increases, specifically, when temperature exceeds 32° C. for neurons initially under room temperature (Shibasaki et al., 2007). Based on the simulation, the surface temperature increases of 8° C. (from 20° C. to 28° C.) under nanosecond light excitation is not sufficient to evoke TRPV4 current by heat alone. These findings collectively show that PAN neural stimulation observed is mainly contributed by the photoacoustic effect.

Since PAN generates acoustic wave with the ultrasonic frequencies, it is likely that PAN mediated stimulation shares the mechanisms of ultrasound neuromodulation. Several possible mechanisms have been proposed for ultrasound neuromodulation, and activation of mechanosensitive ion channels is among the most studied in the literature. Direct binding to TRPV4 enhances stimulation specificity and efficiency, which suggests activation of mechanosensitive channels as a potential mechanism candidate. Nevertheless, other mechanosensitive channels may include TRPC4, Piezo 1, TREK-1 and TRAAK channels. Other possible mechanisms involve transient mechanical disruptions of the neuronal membrane, which includes permeability change induced by membrane sonoporation and capacitive current generated by intramembrane cavitation.

Notably when thermal confinement was met, many nanoparticles, including Au nanoparticles, can also be photoacoustic. The photoacoustic properties of these nanostructures have been only applied for photoacoustic imaging. The semiconducting polymer-based PAN provides a new paradigm for neural modulation through offering three important features compared to other photoacoustic agents. First, COMSOL simulation for Au nanoparticles were compared under a nanosecond laser at the wavelength of 532 nm wavelength to that for PANs. Under the same laser power, the maximum temperature rise is 40.4° C. on Au nanoparticle surface, compared to 8.4° C. on PAN surface. As it produces less temperature rise, avoiding potential thermal toxicity while effectively activating neurons, PAN is of particular interest for neuron stimulation. Second, semiconducting polymer nanoparticles have been shown to have biocompatibility and biodegradability. The results also confirmed that PAN induces minimal cytotoxicity to neurons in vitro. Additionally, through an engineered metabolizing pathway, biodegradation of semiconducting polymer nanoparticles has recently demonstrated in vitro and in vivo, which potentially allows clearance of PAN from the brain after stimulation. Third, PANs provide an exciting opportunity for non-invasive neural modulation and other biological regulation. PANs uniquely absorb NIR-II light. Due to its longer wavelength, NIR-II light has been reported to have sufficient penetration depth in highly scattering medium. Such wavelength has also been demonstrated to have the capability of penetrating human skull, potentially enabling non-surgical brain stimulation through light excitation.

To illustrate the possibility for deep penetration, PANs were embedded in a 5 mm thick brain-mimicking phantom under a mouse skull. Optoacoustic signals were detected from these PANs by nanosecond laser excitation above the skull using photoacoustic tomography. In addition, advances in biophotonics showed that NIR light focusing with approximately 100 μm is possible in brain tissue. PAN neural modulation does not require genetic modification, which makes it suitable for potential clinical applications in human subjects. Additionally, compared to photothermal neuromodulation based on light-absorbing nanoparticles, often with CW laser, PAN mediated stimulation shows no thermal accumulation, which largely eliminates thermally induced tissue damage. Together with potential development in surgical free targeted delivery of PANs to specific regions of a brain, for example, via ultrasound openings of the blood-brain barrier, PANs promise an opportunity of non-genetic and non-surgical brain modulation in live animals and further in human patients.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is intended that the scope of the present disclosure be limited not by this detailed description, but rather by the claims of this application. As will be understood by those familiar with the art, the present disclosure may be embodied in other specific forms without departing from the spirit or essential characteristics thereof. Accordingly, the present disclosure is intended to be illustrative, but not limiting, of the scope of the present disclosure, which is set forth in the following claims.

What is claimed is:

1. A photoacoustic system for neurostimulation comprising:
    a light producing device for producing light of a specific wavelength; and
    at least one nanotransducer adapted to be binded on a surface of a neuron, the at least one nanotransducer converting the light with the specific wavelength into at least one acoustic wave at or near the neuron.

2. The photoacoustic system of claim 1, wherein the specific wavelength is between 800 nm and 1800 nm.

3. The photoacoustic system of claim 1, wherein the light is a light pulse.

4. The photoacoustic system of claim 1, wherein the light producing device is coupled to a tapered fiber for delivery of the light.

5. The photoacoustic system of claim 1, wherein the at least one nanotransducer comprises semiconducting polymer nanoparticles.

6. The photoacoustic system of claim 1, wherein the at least one nanotransducer is a plurality of photoacoustic nanotransducers (PANs) for neural stimulation.

7. The photoacoustic system of claim 1, wherein the at least one nanotransducer is adapted to be implemented in vitro on the neuron.

8. The photoacoustic system of claim 1, wherein the at least one nanotransducer is adapted to be implemented in vivo on the neuron.

9. The photoacoustic system of claim 1, wherein the at least one nanotransducer is injected thru blood to reach the neuron.

10. The photoacoustic system of claim 1, wherein the at least one nanotransducer is adapted to be positioned on the neuron via openings of the blood-brain barrier.

11. The photoacoustic system of claim 1, wherein the light producing device generates heat confined in the at least one nanotransducer.

12. A method for neurostimulation, the method comprising:
    producing light of specific wavelength;
    positioning at least one nanotransducer binded on a surface of a neuron; and
    converting, using the at least one nanotransducer, the light with the specific wavelength into at least one acoustic wave at or near the neuron.

13. The method of claim 12, wherein the specific wavelength is between 800 nm and 1800 nm.

14. The method of claim 12, wherein the light is a light pulse.

15. The method of claim 12, wherein producing the light comprises coupling a light producing device to a tapered fiber for delivery of the light.

16. The method of claim 12, wherein the at least one nanotransducer comprises semiconducting polymer nanoparticles.

17. The method of claim 12, wherein the at least one nanotransducer is a plurality of photoacoustic nanotransducers (PANs) for neural stimulation.

18. The method of claim 12, further comprising implementing the at least one nanotransducer in vitro on the neuron.

19. The method of claim 12, further comprising implementing the at least one nanotransducer in vivo on the neuron.

20. The method of claim 12, further comprising injecting the at least one nanotransducer thru blood to reach the neuron.

21. The method of claim 12, further comprising positioning the at least one nanotransducer on the neuron via openings of the blood-brain barrier.

22. The method of claim 12, further comprising generating, using the light producing device, heat confined in the at least one nanotransducer.

23. A system for neurostimulation comprising:
a light producing device producing light of specific wavelength; and
at least one nanotransducer adapted to be binded on a surface of a neuronal membrane and targeting at least one mechanosensitive ion channel, the at least one nanotransducer converting the light with the specific wavelength into at least one acoustic wave perturbing the at least one mechanosensitive ion channel directly.

24. The system of claim 23, wherein the specific wavelength is between 800 nm and 1800 nm.

25. The system of claim 23, wherein the light is a light pulse.

26. The system of claim 23, wherein the light producing device is coupled to a tapered fiber for delivery of the light.

27. The system of claim 23, wherein the at least one nanotransducer is a plurality of photoacoustic nanotransducers (PANs) for neural stimulation.

28. The system of claim 23, wherein the at least one nanotransducer is injected thru blood to reach the neuron.

29. The system of claim 23, wherein the at least one nanotransducer is adapted to be positioned on the neuron via openings of the blood-brain barrier.

30. The system of claim 23, wherein the light producing device generates heat confined in the at least one nanotransducer.

* * * * *